(12) United States Patent
Hidai

(10) Patent No.: US 7,517,655 B2
(45) Date of Patent: Apr. 14, 2009

(54) PROTEIN CAPABLE OF DEPOSITION ONTO EXTRACELLULAR MATRIX

(75) Inventor: Chiaki Hidai, Tokyo (JP)

(73) Assignee: Nihon University, Tokyo (JP)

( * ) Notice: Subject to any disclaimer, the term of this patent is extended or adjusted under 35 U.S.C. 154(b) by 177 days.

(21) Appl. No.: 10/563,166

(22) PCT Filed: Jun. 30, 2004

(86) PCT No.: PCT/JP2004/009616

§ 371 (c)(1),
(2), (4) Date: Apr. 6, 2006

(87) PCT Pub. No.: WO2005/001093

PCT Pub. Date: Jan. 6, 2005

(65) Prior Publication Data

US 2006/0199184 A1 Sep. 7, 2006

(30) Foreign Application Priority Data

Jun. 30, 2003 (JP) ............................. 2003-188598

(51) Int. Cl.
*G01N 33/53* (2006.01)
*C07K 4/00* (2006.01)
*C07K 14/00* (2006.01)

(52) U.S. Cl. .................. 435/7.1; 530/324; 530/350; 530/810

(58) Field of Classification Search ............... None
See application file for complete search history.

(56) References Cited

U.S. PATENT DOCUMENTS

| 5,874,562 | A | 2/1999 | Quertermous et al. |
| 5,877,281 | A | 3/1999 | Quertermous et al. |
| 6,812,339 | B1 * | 11/2004 | Venter et al. ............. 536/24.31 |
| 6,905,688 | B2 | 6/2005 | Rosen et al. |
| 7,041,801 | B1 | 5/2006 | Quertermous et al. |

FOREIGN PATENT DOCUMENTS

| EP | 0854883 | 7/1998 |
| WO | WO 96/40769 | 12/1996 |
| WO | WO 02/36826 | 5/2002 |

OTHER PUBLICATIONS

Burgess et al .Possible dissociation of the heparin-binding and mitogenic activities of heparin-binding (acidic fibroblast) growth factor-1 from its receptor-binding activities by site-directed mutagenesis of a single lysine residue. J Cell Biol. 111:2129-2138, 1990.*
Wang et al. A Single Amino Acid Determines Lysophospholipid Specificity of the S1P1 (EDG1) and LPA1 (EDG2) Phospholipid Growth Factor Receptors J. Biol. Chem., vol. 276, Issue 52, 49213-49220, Dec. 28, 2001.*
Bowie et al. Science, 247:1306-1310, 1990.*
Ezekowitz RA. Local opsonization for apoptosis? *Nat Immunol.* 2002 Jun;3(6):510-512.
Hanayama et al. Expression of developmental endothelial locus-1 in a subset of macrophages of engulfment of apoptotic cells. *J Immunol.* Mar. 15, 2004; 172(6):3876-3882.
Hanayama et al. Identification of a factor that links apoptotic cells to phagocytes. *Nature.* May 9, 2002;417(6885):182-187.
Hidai et al., 1998 "Cloning and characterization of developmental endothelial locus-1: An embryonic endothelial cell protein that binds the αvβ3 integrin receptor" *Genes & Development* 12:21-33.

* cited by examiner

*Primary Examiner*—Maher M Haddad
(74) *Attorney, Agent, or Firm*—Jones Day

(57) ABSTRACT

The present invention provides the following partial fragment (a) or (b) of developmentally regulated endothelial cell locus-1 (Del-1) protein: (a) a protein consisting of the amino acid sequence as shown in SEQ ID NO: 6, 8, 10, 12, 18 or 24; or (b) a protein which consists of the amino acid sequence as shown in SEQ ID NO: 6, 8, 10, 12, 18 or 24 having deletion, substitution or addition of one or several amino acids, and has deposition activity onto extracellular matrix.

4 Claims, 7 Drawing Sheets

Figure 1:
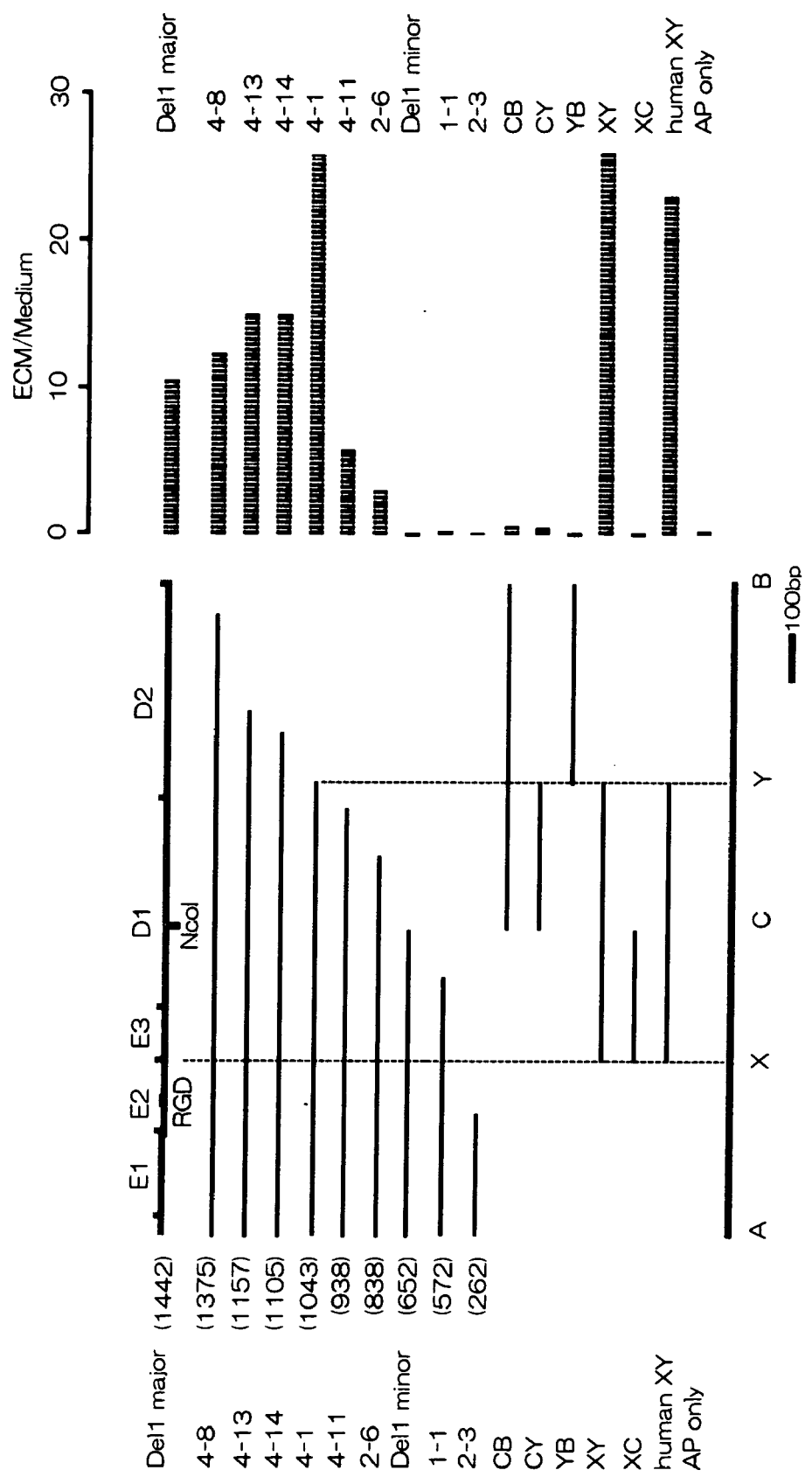

FIG. 7
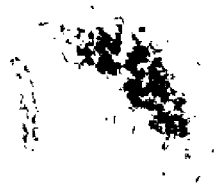

PROTEIN CAPABLE OF DEPOSITION ONTO EXTRACELLULAR MATRIX

This application is the United States National Stage of International Application No. PCT/JP2004/009616, filed Jun. 30, 2004, which is incorporated by reference herein in its entirety.

TECHNICAL FIELD

The present invention relates to a protein capable of deposition onto extracellular matrix, which is a partial fragment of developmentally regulated endothelial cell locus-1 (Del-1) protein. The present invention also relates to a method of identifying the site of deposition onto extracellular matrix using the above-described partial fragment, and a method of recovering a molecule of interest (e.g., alkaline phosphatase) fused to Del-1 protein.

BACKGROUND ART

Del-1 (developmentally regulated endothelial cell locus-1) protein (sometimes just referred to as "Del-1" or the "full-length Del-1") is a protein which has EGF (epithelial growth factor)-like domains and discoidin-I-like domains. This protein is an extracellular matrix protein and is known to bind to a protein called $\alpha v \beta 3$ integrin receptor or $\alpha v \beta 5$ integrin receptor on the surfaces of vascular endothelial cells via the EGF-like domain to thereby promote adhesion of the endothelial cells onto extracellular matrix (Hidai, C. et al., GENES & DEVELOPMENT 12:21-33, 1998).

Recently, a gene encoding the full-length Del-1 has been cloned. It is presumed that the full-length Del-1 is capable of binding, via a part or the entire region thereof, to proteoglycan present in extracellular matrix. A method based on this binding is known in which the full-length Del-1 is expressed; a specific molecule (e.g., a protein or proteoglycan) is bound to the resultant full-length Del-1; and then the molecule bound to the full-length Del-1 (e.g., a protein or proteoglycan) is recovered (see, for example, Japanese Unexamined Patent Publication/PCT No. H11-507527).

Therefore, identification of these binding sites and analysis of the mode of binding are important for recovering molecules of interest and investigating into molecules which bind to the full-length Del-1.

However, since the ability of the full-length Del-1 to deposit onto extracellular matrix is not so high, molecules of interest bound to the full-length Del-1 could not have been recovered sufficiently.

DISCLOSURE OF THE INVENTION

It is an object of the present invention to provide a partial fragment of Del-1 comprising a region capable of efficiently adhering onto extracellular matrix.

As a result of extensive and intensive researches toward the solution of the above problem, the present inventor has found that regions neighboring the discoidin-I-like domains efficiently deposit onto extracellular matrix. Thus, the present invention has been achieved.

The present invention relates to the following.
(1) A protein selected from the following (a) or (b):
  (a) a protein comprising the amino acid sequence as shown in SEQ ID NO: 18 or 24;
  (b) a protein which comprises the amino acid sequence as shown in SEQ ID NO: 18 or 24 having deletion, substitution or addition of one or several amino acids, and has deposition activity onto extracellular matrix.
(2) A protein selected from the following (a) or (b):
  (a) a protein consisting of the amino acid sequence as shown in SEQ ID NO: 6, 8, 10, 12, 18 or 24;
  (b) a protein which consists of the amino acid sequence as shown in SEQ ID NO: 6, 8, 10, 12, 18 or 24 having deletion, substitution or addition of one or several amino acids, and has deposition activity onto extracellular matrix.
(3) A protein selected from the following (a) or (b):
  (a) a protein comprising the amino acid sequence as shown in SEQ ID NO: 14;
  (b) a protein which comprises the amino acid sequence as shown in SEQ ID NO: 14 having deletion, substitution or addition of one or several amino acids, and has inhibitory activity against deposition onto extracellular matrix.
(4) A gene encoding a protein selected from the following (a) or (b):
  (a) a protein comprising the amino acid sequence as shown in SEQ ID NO: 18 or 24;
  (b) a protein which comprises the amino acid sequence as shown in SEQ ID NO: 18 or 24 having deletion, substitution or addition of one or several amino acids, and has deposition activity onto extracellular matrix.
(5) A gene encoding a protein selected from the following (a) or (b):
  (a) a protein consisting of the amino acid sequence as shown in SEQ ID NO: 6, 8, 10, 12, 18 or 24;
  (b) a protein which consists of the amino acid sequence as shown in SEQ ID NO: 6, 8, 10, 12, 18 or 24 having deletion, substitution or addition of one or several amino acids, and has deposition activity onto extracellular matrix.
(6) A gene encoding a protein selected from the following (a) or (b):
  (a) a protein comprising the amino acid sequence as shown in SEQ ID NO: 14;
  (b) a protein which comprises the amino acid sequence as shown in SEQ ID NO: 14 having deletion, substitution or addition of one or several amino acids, and has inhibitory activity against deposition onto extracellular matrix.
(7) A gene comprising a DNA selected from the following (a) or (b):
  (a) a DNA comprising the nucleotide sequence as shown in SEQ ID NO: 17 or 23;
  (b) a DNA which hybridizes to a DNA comprising a nucleotide sequence complementary to a DNA consisting of the nucleotide sequence as shown in SEQ ID NO: 17 or 23 under stringent conditions, and encodes a protein having deposition activity onto extracellular matrix.
(8) A gene comprising a DNA selected from the following (a) or (b):
  (a) a DNA consisting of the nucleotide sequence as shown in SEQ ID NO: 5, 7, 9, 11, 17 or 23;
  (b) a DNA which hybridizes to a DNA consisting of a nucleotide sequence complementary to a DNA consisting of the nucleotide sequence as shown in SEQ ID NO: 5, 7, 9, 11, 17 or 23 under stringent conditions, and encodes a protein having deposition activity onto extracellular matrix.
(9) A gene comprising a DNA selected from the following (a) or (b):
  (a) a DNA comprising the nucleotide sequence as shown in SEQ ID NO: 13;

(b) a DNA which hybridizes to a DNA comprising a nucleotide sequence complementary to a DNA consisting of the nucleotide sequence as shown in SEQ ID NO: 13 under stringent conditions, and encodes a protein having inhibitory activity against deposition onto extracellular matrix.

(10) A recombinant vector comprising the gene according to any one of (4) to (9) above.

(11) A transformant comprising the recombinant vector according to (10) above.

(12) A method of producing a partial fragment of Del-1 protein, comprising culturing the transformant according to (11) above and collecting the partial fragment of Del-1 protein from the resultant culture.

(13) A method of identifying a site in extracellular matrix at which the protein according to any one of (1) to (3) above deposits, comprising reacting the above protein with extracellular matrix.

(14) A reagent for identifying a site of deposition in extracellular matrix, comprising the protein according to any one of (1) to (3) above.

(15) A fusion protein composed of the protein according to any one of (1) to (3) above linked to a molecule of interest to be expressed.

(16) A drug delivery system comprising the fusion protein according to (15) above.

(17) A gene encoding a fusion protein, wherein the gene according to any one of (4) to (9) above is linked to a gene encoding a molecule of interest to be expressed.

(18) A recombinant vector comprising the gene according to (17) above.

(19) A transformant comprising the recombinant vector according to (18) above.

(20) A method of producing a fusion protein composed of a partial fragment of Del-1 protein and a molecule of interest to be expressed, comprising culturing the transformant according to (19) above and collecting the fusion protein from the resultant culture.

(21) A method of recovering a molecule of interest, comprising allowing the fusion protein according to (15) above to deposit onto extracellular matrix and collecting the molecule of interest.

(22) A method of allowing a molecule of interest to deposit, comprising the following steps:
  (a) a step of producing a fusion protein composed of the molecule of interest to be expressed and a partial fragment of Del-1 protein by culturing the transformant according to (19) above; and
  (b) a step of allowing the fusion protein to deposit onto extracellular matrix.

(23) A method of recovering a molecule of interest, comprising the following steps:
  (a) a step of producing a fusion protein composed of the molecule of interest to be expressed and a partial fragment of Del-1 protein by culturing the transformant according to (19) above;
  (b) a step of allowing the fusion protein to deposit onto extracellular matrix; and
  (c) a step of cutting off the protein of interest from the fusion protein to thereby collect the molecule of interest.

(24) A method of regulating deposition activity onto extracellular matrix, comprising reacting a fragment within the amino acid sequence as shown in SEQ ID NO: 2 comprising an active center region and a positive regulation region and/or a fragment within the amino acid sequence as shown in SEQ ID NO: 2 comprising an active center region and a negative regulation region with extracellular matrix.

(25) The method according to (24) above, wherein the amino acid sequence of the active center region is as shown in SEQ ID NO: 4.

(26) The method according to (24) above, wherein the amino acid sequence of the positive regulation region is as shown in SEQ ID NO: 20.

(27) The method according to (24) above, wherein the amino acid sequence of the negative regulation region is as shown in SEQ ID NO: 22.

According to the present invention, Del-1 partial fragments are provided. Since the proteins expressed from these Del-1 partial fragments have deposition activity onto extracellular matrix, use of the Del-1 partial fragment allows a molecule of interest linked to the protein expressed from the Del-1 partial fragment to deposit onto extracellular matrix efficiently. Also, it is possible to recover or remove the molecule of interest by means of this deposition.

By allowing a molecule of interest to deposit onto extracellular matrix using the Del-1 partial fragment of the invention, it is possible to concentrate and localize the molecule of interest in a target tissue. In particular, by preventing the molecule of interest from flowing into plasma, it is possible to prevent the migration of that molecule into other tissues.

The Del-1 partial fragments of the invention include those fragments which express proteins having a function of inhibiting the deposition onto extracellular matrix. Therefore, by increasing/decreasing the deposition activity with a combination of a fragment having deposition activity and a fragment having deposition inhibitory activity, it is possible to control the recovery, removal, concentration, etc. of a molecule of interest.

BRIEF DESCRIPTION OF THE DRAWINGS

FIG. 1 is a diagram showing an outline of the nucleotide sequences of the Del-1 partial fragments of the invention and the results of measurement of deposition activities of individual fragments using alkaline phosphatase activity.

FIG. 2 is a diagram showing the deposition activities of the Del-1 partial fragments of the invention.

FIG. 3 is a diagram showing AP/Lac ratios in plasma samples taken from individual livers.

FIG. 4 is a diagram showing AP/Lac ratios in hepatic tissue samples taken from individual livers.

FIG. 5 is a diagram showing the results of alkaline phosphatase staining of hepatic tissue samples taken from individual livers.

FIG. 6 is a diagram showing the results of Western blotting.

FIG. 7 is a diagram showing the results of alkaline phosphatase recovery.

BEST MODE FOR CARRYING OUT THE INVENTION

The present invention relates to partial fragments of the full-length Del-1 protein which comprise a region that specifically binds to extracellular matrix. Specifically, the present invention relates to Del-1 deposition proteins and Del-1 deposition inhibitory proteins (sometimes, simply referred to as "Del-1 partial fragments"). The Del-1 partial fragments of the invention are obtained by truncating the full-length Del-1 into fragments with varied lengths and characterized by having deposition activity onto extracellular matrix.

The Del-1 partial fragment of the invention comprises amino acids encoded by a region of the full-length Del-1 gene (SEQ ID NO: 1) spanning at least from position 1270 to position 1662 (corresponding to an amino acid sequence from position 218 to position 348 of the amino acid sequence as shown in SEQ ID NO: 2). The nucleotide sequence of this region is shown in SEQ ID NO: 3 and the amino acid sequence encoded by this nucleotide sequence is shown in SEQ ID NO: 4. The Del-1 partial fragment of the invention comprising the above-described region has the nucleotide sequence as shown in SEQ ID NO: 5, 7, 9, 11, 13, 15 or 17. The amino acid sequences encoded by these nucleotide sequences are shown in SEQ ID NOS: 6, 8, 10, 12, 14, 16 and 18, respectively.

It is presumed that the Del-1 partial fragment described above is capable of binding to proteoglycan in view of the amino acid sequence encoding the partial fragment.

For detecting the full-length Del-1 protein or Del-1 partial fragments, a method using alkaline phosphatase is employed. Briefly, by allowing cells to express a fusion protein composed of the full-length Del-1 protein to which alkali phosphatase is fused to the N terminus by genetic recombination, alkaline phosphatase activity can be confirmed in culture supernatant as well as extracellular matrix.

In the present invention, in addition to the above-described detection method using alkaline phosphatase, it is also possible to use Western blotting for the detection of Del-1 partial fragments, etc. Specifically, a nucleotide sequence encoding a fusion protein composed of alkaline phosphatase and the full-length Del-1 or a Del-1 partial fragment is introduced into cos7 cells. The cells are cultured for a specific period of time, and then the culture medium and extracellular matrix are collected and subjected to Western blotting for detection. As controls, laminin and albumin may be used, for example. In the Western blotting, in order to improve the detection sensitivity for the Del-1 protein or Del-1 partial fragment in the culture supernatant, the volume of culture medium used in the method may be increased and the protein may be concentrated.

Although either of the above detection methods may be used, the method using alkaline phosphatase is preferable.

In the present invention, the full-length Del-1 (which is known) was truncated by various methods to prepare Del-1 partial fragments of the invention. The resultant partial fragments were detected by the above-described detection method using alkaline phosphatase and subjected to Western blotting to examine the ability to deposit onto extracellular matrix. Further, the site of deposition of the Del-1 partial fragment onto extracellular matrix was identified; and immobilization of the Del-1 partial fragment onto a specific site in the living body was preformed. Further, the expression product of a gene of interest was recovered using the Del-1 partial fragment.

Hereinbelow, embodiments of the present invention will be described specifically.

1. DNAs Encoding Del-1 Partial Fragments

Del-1 partial fragments can be obtained by truncating the DNA encoding the full-length Del-1 protein into various lengths and then expressing these truncated DNAs.

The full-length Del-1 gene may be cloned by the known method (Hidai, C. et al., GENES & DEVELOPMENT 12:21-33, 1998). Briefly, an exon is obtained from a genomic library by exon trapping. Using this exon, cDNA of Del-1 can be cloned.

For example, a fragment from a genomic clone is inserted into a splicing vector to thereby cause splicing at the time of transcription of mRNA. Subsequently, the spliced mRNA is reverse-transcribed and amplified, followed by sequencing of the exon.

The resultant exon is used as a probe to probe a cDNA library for the DNA of interest, or used in designing gene specific primers for 5'-RACE or 3'-RACE. RACE may be performed with commercial kits (e.g., Marathon™ cDNA Amplification Kit; Clontech).

The determination of the nucleotide sequence of cDNA may be performed by any of known methods. Usually, sequencing is performed with an automated DNA sequencer.

The thus obtained nucleotide sequence of the full-length cDNA is shown in SEQ ID NO: 1. The amino acid sequence encoded by the nucleotide sequence as shown in SEQ ID NO: 1 is shown in SEQ ID NO: 2.

One of the truncated Del-1 partial fragments of the invention comprises an amino acid sequence spanning from positions 1 to 348 of the amino acid sequence as shown in SEQ ID NO: 2. This partial fragment can be obtained by serially deleting a DNA having the nucleotide sequence as shown in SEQ ID NO: 1 from the 3' end with exonuclease III and mung bean nuclease. The 3' terminal DNA deleted is determined by the reaction time of exonuclease III. In this method, a commercial enzyme (e.g., Exonuclease III; Takara Bio) may be used.

A schematic diagram showing the full-length Del-1 (Del-1 major), truncated Del-1 partial fragments of the invention and amino acid sequences affecting the deposition activities of these partial fragments is shown in the left upper part of FIG. 1.

In FIG. 1, the following partial fragments have the following amino acid sequences in the amino acid sequence as shown in SEQ ID NO: 2. CY has the amino acid sequence of a region spanning from positions 218 to 348 (SEQ ID NO: 4); 4-1 has the amino acid sequence of a region spanning from positions 1 to 348 (SEQ ID NO: 6); 4-14 has the amino acid sequence of a region spanning from positions 1 to 368 (SEQ ID NO: 10); 4-13 has the amino acid sequence of a region spanning from positions 1 to 385 (SEQ ID NO: 12); CB has the amino acid sequence of a region spanning from positions 218 to 480 (SEQ ID NO: 14); and XY has the amino acid sequence of a region spanning from positions 123 to 348 (SEQ ID NO: 18).

DNAs encoding these Del-1 partial fragments (designated "DNAs of the invention") have the following nucleotide sequences in the nucleotide sequence as shown in SEQ ID NO: 1. CY has the nucleotide sequence of a region spanning from positions 1270 to 1662 (393 bp, SEQ ID NO: 3); 4-1 has the nucleotide sequence of a region spanning from positions 619 to 1662 (1044 bp, SEQ ID NO: 5); 4-14 has the nucleotide sequence of a region spanning from positions 619 to 1722 (1104 bp, SEQ ID NO: 9); 4-13 has the nucleotide sequence of a region spanning from positions 619 to 1773 (1155 bp, SEQ ID NO: 11); CB has the nucleotide sequence of a region spanning from positions 1270 to 2058 (789 bp, SEQ ID NO: 13); and XY has the nucleotide sequence of a region spanning from positions 985 to 1662 (678 bp, SEQ ID NO: 17).

Further, human XY (SEQ ID NO: 24) in human full-length Del-1 corresponding to mouse fragment XY (SEQ ID NO: 18) was also measured for its deposition activity. The DNA encoding human XY has the nucleotide sequence as shown in SEQ ID NO: 23.

Although not shown in FIG. 1, 4-15 and DE are also truncated Del-1 partial fragments of the invention; 4-15 has the amino acid sequence of a region spanning from 1 to 365 of the amino acid sequence as shown in SEQ ID NO: 2 (SEQ ID NO: 8) and DE has the amino acid sequence of a region spanning from 218 to 319 of the amino acid sequence as shown in SEQ ID NO: 2 (SEQ ID NO: 16). DNAs encoding these amino acid sequences have the nucleotide sequence of a region spanning from positions 619 to 1713 of the nucleotide sequence as shown in SEQ ID NO: 1 (1095 bp, SEQ ID NO: 7) for 4-15 and the nucleotide sequence of a region spanning from positions 1270 to 1575 of the nucleotide sequence as shown in SEQ ID NO: 1 (306 bp, SEQ ID NO: 15) for DE.

In FIG. 1, XC has the amino acid sequence of a region spanning from positions 123 to 217 (SEQ ID NO: 20) and YB has the amino acid sequence of a region spanning from positions 349 to 480 (SEQ ID NO: 22) as an amino acid sequence improving or reducing the deposition activity of the Del-1 partial fragment of the invention. DNAs encoding these amino acid sequences have the nucleotide sequence of a region spanning from positions 985 to 1269 (285 bp, SEQ ID NO: 19) for XC and the nucleotide sequence of a region spanning from positions 1663 to 2058 (396 bp, SEQ ID NO: 21) for YB.

Further, the partial fragments of the present invention comprise CY represented by an amino acid sequence spanning at least from position 218 to position 348 (SEQ ID NO: 4) of the amino acid sequence as shown in the above-mentioned SEQ ID NO: 2. In one embodiment of the invention, the partial fragment of the invention comprises a protein in which a plurality of the amino acid sequences spanning at least from position 218 to position 348 (SEQ ID NO: 4) of the amino acid sequence as shown in the above-mentioned SEQ ID NO: 2 are connected. This region is the center region having deposition activity onto extracellular matrix. The above-described CY is encoded by a region spanning from positions 1270 to 1662 (SEQ ID NO: 3) of the nucleotide sequence as shown in SEQ ID NO: 1.

The amino acid sequence as shown in SEQ ID NO: 20 (XC) improves deposition activity onto extracellular matrix and is a positive regulation region for the deposition activity. On the other hand, the amino acid sequence as shown in SEQ ID NO: 22 (YB) reduces deposition activity onto extracellular matrix and is a negative regulation region for the deposition activity. The "positive regulation region" means a region which does not cause deposition activity by itself but is capable of causing deposition activity when the center region CY is included in the relevant fragment. The "negative regulation region" means a region whose presence, as a whole or as a part, causes reduction in deposition activity regardless of the presence of center region CY or positive regulation region XC, resulting in increase in soluble fraction.

The regions contained in the Del-1 partial fragments of the invention are summarized in the following Table 1.

TABLE 1

| Designation | Region* | | Type | SEQ ID NO: |
|---|---|---|---|---|
| Full-length Del-1 | | | DNA | 1 |
| Full-length Del-1 | 619-2061 | | Protein | 2 |
| CY | 1270-1662 | Center region | DNA | 3 |
| CY | 218-348 | Center region | Protein | 4 |
| 4-1 | 619-1662 | Comprising center region + positive regulation region | DNA | 5 |
| 4-1 | 1-348 | Comprising center region + positive regulation region | Protein | 6 |
| 4-15 | 619-1713 | Center region + positive regulation region | DNA | 7 |
| 4-15 | 1-365 | Comprising center region + positive regulation region | Protein | 8 |
| 4-14 | 619-1722 | Center region + positive regulation region | DNA | 9 |
| 4-14 | 1-368 | Center region + positive regulation region | Protein | 10 |
| 4-13 | 619-1773 | Center region + positive regulation region | DNA | 11 |
| 4-13 | 1-385 | Center region + positive regulation region | Protein | 12 |
| CB | 1270-2058 | Center region + negative regulation region | DNA | 13 |
| CB | 218-480 | Center region + negative regulation region | Protein | 14 |
| DE | 1270-1575 | | DNA | 15 |
| DE | 218-319 | | Protein | 16 |
| XY | 985-1662 | Center region + positive regulation region | DNA | 17 |
| XY | 123-348 | Center region + positive regulation region | Protein | 18 |
| XC | 985-1269 | Positive regulation region | DNA | 19 |
| XC | 123-217 | Positive regulation region | Protein | 20 |
| YB | 1663-2058 | Negative regulation region | DNA | 21 |
| YB | 349-480 | Negative regulation region | Protein | 22 |
| human XY | | Center region + positive regulation region | DNA | 23 |
| human XY | | Center region + positive regulation region | Protein | 24 |

*Regions are expressed with nucleotide positions for DNAs and with amino acid positions for proteins.

Once the regions to be included in a partial fragment are determined, primers are designed so that those regions are amplified. Then, a DNA encoding the partial fragment can be readily obtained by PCR using the DNA encoding Del-1 as a template.

In the present invention, it should be noted that as long as the protein consisting of the above-described amino acid sequence for the Del-1 partial fragment has deposition activity onto extracellular matrix, the amino acid sequence may have mutations, such as deletion, substitution or addition, in at least one, preferably one or several amino acids.

For example, one or several amino acids (e.g., 1 to 10, preferably 1 to 5 amino acids) may be deleted from the amino acid sequence as shown in SEQ ID NO: 6, 8, 10, 12, 18 or 24; one or several amino acids (e.g., 1 to 10, preferably 1 to 5 amino acids) may be added to the amino acid sequence as shown in SEQ ID NO: 6, 8, 10, 12, 18 or 24; and one or several amino acids (e.g., 1 to 10, preferably 1 to 5 amino acids) may be substituted with other amino acids in the amino acid sequence as shown in SEQ ID NO: 6, 8, 10, 12, 18 or 24. Therefore, genes encoding proteins comprising the above mutation-introduced amino acid sequences are also included in the gene of the invention as long as the proteins have deposition activity onto extracellular matrix.

It should be also noted that as long as the protein consisting of the above-described amino acid sequence for the Del-1 partial fragment has a function to inhibit deposition activity onto extracellular matrix, the amino acid sequence may have mutations, such as deletion, substitution or addition in at least one, preferably one or several amino acids.

For example, one or several amino acids (e.g., 1 to 10, preferably 1 to 5 amino acids) may be deleted from the amino acid sequence as shown in SEQ ID NO: 14 which represents CB region; one or several amino acids (e.g., 1 to 10, preferably 1 to 5 amino acids) may be added to the amino acid sequence as shown in SEQ ID NO: 14; and one or several amino acids (e.g., 1 to 10, preferably 1 to 5 amino acids) may be substituted with other amino acids in the amino acid sequence as shown in SEQ ID NO: 14. Therefore, genes encoding proteins comprising the above mutation-introduced amino acid sequences are also included in the gene of the invention as long as the proteins have activity to inhibit deposition onto extracellular matrix.

Introduction of the above-described mutations such as deletion, substitution or addition may be performed with a kit utilizing site-directed mutagenesis techniques, e.g., GeneTailor™ Site-Directed Mutagenesis System (Invitrogen) or TaKaRa Site-Directed Mutagenesis System (Mutan-K, Mutan-Super Express Km; Takara Bio).

Further, in the present invention, a DNA which is hybridizable to a DNA consisting of a nucleotide sequence complementary to the DNA encoding the above-described Del-1 partial fragment (SEQ ID NO: 5, 7, 9, 11, 17 or 23) under stringent conditions and encodes a protein having binding activity to extracellular matrix is also included in the gene of the invention. Stringent conditions means, for example, salt (sodium) concentration is 150-900 mM and temperature is 55-75° C.; preferably, salt (sodium) concentration is 150-200 mM and temperature is 60-70° C.

Further, in the present invention, a DNA which is hybridizable to a DNA consisting of a nucleotide sequence complementary to the DNA encoding the above-described Del-1 partial fragment (SEQ ID NO: 13) under stringent conditions and encodes a protein having activity to inhibit deposition onto extracellular matrix is also included in the gene of the invention.

The term "extracellular matrix" (ECM) refers to a biological structure present outside of cells in animal tissues and means an assembly of biopolymers which were synthesized within cells and secreted/accumulated outside of the cells. Major components of extracellular matrix are collagen, elastin, proteoglycan, glycosaminoglycan and sugar proteins. "Deposition activity" means the activity of the entire region or a partial fragment of Del-1 binding to extracellular matrix. Some partial fragments have higher deposition activity than the full-length Del-1, and some have lower deposition activity than the full-length Del-1. Some fragments shorter than the full-length Del-1 but having equivalent deposition activity are also included. The "activity to inhibit deposition onto extracellular matrix" means the activity of reducing deposition activity and thus increasing soluble fraction, which is caused by the presence of a negative regulation region regardless of the presence of center region CY or positive regulation region XC. Measurement of deposition activity or activity to inhibit deposition onto extracellular matrix may be performed, for example, as described below.

Briefly, a DNA encoding a marker such as alkaline phosphatase is linked to the DNA of the invention. The resultant DNA is introduced into a specific cell (e.g., cos7 cells, CHO cells, NIH3T3 cells, etc.), which is then cultured. After the culture supernatant and cells are removed from the culture dish, the substrate of alkaline phosphatase is added to the extracellular matrix remaining in the dish for color development to thereby measure deposition activity. Since a marker (alkaline phosphatase) is linked to the Del-1 partial fragment, when the Del-1 partial fragment deposits onto extracellular matrix, it is possible to measure the binding activity and also to identify the site of binding using the marker as an indicator. For example, when a soluble alkaline phosphatase substrate is used, the substrate develops a color (e.g., yellow). Thus, deposition activity can be easily determined by measuring absorbance at a specific wavelength. Alternatively, when an alkaline phosphatase of deposition property is used, the site of deposition develops a color (e.g., purple). Thus, the deposition site can be easily identified by microscopic observation or the like.

The marker useful in the invention is not limited to alkaline phosphatase. GFP or a variation thereof, a tag such as myc or His, GST protein, an isotope, a biotinylated protein or the like may also be used. Alternatively, it is possible to perform an assay using a reporter gene such as chloramphenicol acetyltransferase (CAT) gene, luciferase gene, or β galactosidase gene.

2. Preparation of Recombinant Vectors and Transformants Comprising the DNA of the Invention (1) Preparation of Recombinant Vectors Comprising the DNA Recombinant vectors comprising the DNA of the invention can be obtained by linking (introducing) the DNA of the invention to an appropriate vector. The vector to which the DNA of the invention is to be inserted is not particularly limited as long as it is capable of replication in a host. For example, plasmid DNA, phage DNA, virus or the like may be used.

As plasmid DNA, *Escherichia coli*-derived plasmids, *Bacillus subtilis*-derived plasmids, yeast-derived plasmid and the like may be enumerated. As phage DNA, λphage and the like may be enumerated. As virus, adenovirus, retrovirus and the like may be enumerated.

The vector of the invention may contain, if desired, cis elements such as enhancers, splicing signals, poly(A) addition signals, selection markers, ribosome binding sequences (SD sequences) or the like in addition to the DNA of the invention. As the selection marker, dihydrofolate reductase gene, ampicillin resistance gene, neomycin resistance gene or the like may be enumerated.

(2) Preparation of Transformants

The transformant of the invention may be obtained by introducing the recombinant vector of the invention into a host so that the gene of interest can be expressed. The host is not particularly limited as long as it can express the DNA of the invention. Specific examples of hosts which may be used in the invention include well-known bacteria, yeasts, animal cells and insect cells. Alternatively, experimental animals such as mouse, domestic animals such as pig, plants such as rice or maize, and the like may be used.

When a bacterium is used as a host, the recombinant vector of the invention is capable of autonomous replication in the host and, at the same time, may also comprise a promoter, a ribosome binding sequence, the DNA of the invention and a transcription termination sequence. Specific examples of bacteria which may be used in the invention include *Escherichia coli* and *Bacillus subtilis*. As a promoter, trp promoter, lac promoter, PL promoter, PR promoter or the lime may be used. The method of introducing the recombinant vector into a bacterium is not particularly limited. For example, the calcium ion method or electroporation may be used.

When a yeast is used as the host, *Saccharomyces cerevisiae*, *Schizosaccharomyces pombe* or the like may be used. A promoter which may be used in this case is not particularly limited. Any promoter may be used as long as it can direct the expression of the DNA in yeast. For example, gal1 promoter, gal10 promoter, heat shock protein promoter, MFα1 promoter, PHO5 promoter, PGK promoter, GAP promoter, ADH promoter, or the like may be enumerated. As a method of introducing the recombinant vector into the yeast, electroporation, the spheroplast method, the lithium acetate method, or the like may be enumerated.

When an animal cell is used as the host, simian cells (cos7 cells), Vero cells, Chinese hamster ovary cells (CHO cells), mouse L cells, rat GH3 cells, human FL cells or HEK293 cells, or the like may be used. As a promoter, SRα promoter, SV40 promoter, LTR promoter, β-actin promoter, or the like may be used. As a method for introducing the recombinant vector into an animal cell, electroporation, the calcium phosphate method, lipofection, or the like may be enumerated.

When an insect cell is used as the host, Sf9 cells, Sf21 cells, or the like may be used. As a method for introducing the recombinant vector into an insect cell, the calcium phosphate method, lipofection, electroporation, or the like may be used.

Gene transfer into animals or plants may be performed, for example, by methods using a virus vector or lipofection. It is also possible to introduce a gene into germ line cells or ES cells to thereby create genetically modified animals.

3. Production of the Del-1 Partial Fragment of the Invention

The Del-1 partial fragment of the invention can be obtained by culturing or breeding the above-described transformant and recovering the fragment from the resultant culture or breeding product. The term "culture" means any of the following materials: culture supernatant, cultured cells, cultured microorganisms, or disrupted materials from cells or microorganisms. The term "breeding product" means any of the following materials: bodies, tissues, secreted materials or excreta of animals or plants, or products obtained by processing these materials.

Cultivation of the transformant of the invention is carried out in accordance with conventional methods commonly used for culturing hosts.

As a medium to culture the transformant obtained from a microorganism host such as bacterium or yeast, either a natural of synthetic medium may be used as long as it contains carbon sources, nitrogen sources and inorganic salts assimilable by the microorganism and is capable of efficient cultivation of the transformant.

As carbon sources, carbohydrates such as glucose, fructose, sucrose, starch; organic acids such as acetic acid, propionic acid; and alcohols such as ethanol and propanol may be used.

As nitrogen sources, ammonia; ammonium salts of inorganic or organic acids such as ammonium chloride, ammonium sulfate, ammonium acetate, ammonium phosphate; Peptone; meat extract; corn steep liquor and the like may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Usually, cultivation is carried out under aerobic conditions (such as shaking culture or aeration agitation culture) at 37° C. for 12 to 24 hours. Adjustment of the pH is carried out using an inorganic or organic acid, an alkali solution or the like.

When a microorganism transformed with an expression vector containing an inducible promoter is cultured, an inducer may be added to the medium, if necessary. For example, when a microorganism transformed with an expression vector containing lac promoter is cultured, isopropyl-β-D-thiogalactoside (IPTG) or the like may be added to the medium.

As a medium to culture a transformant obtained from an animal cell as a host, commonly used RPMI-1640 medium or DMEM medium, or one of these media supplemented with fetal bovine serum, etc. may be used.

Usually, cultivation is carried out in the presence of 5% $CO_2$ at 37° C. for 1 to 4 days. During the cultivation, antibiotics such as kanamycin or penicillin may be added to the medium, if necessary.

After the cultivation, the protein of the invention is extracted by disrupting the microorganisms or cells when the protein is produced within the microorganisms or cells. When the protein of the invention is produced outside the microorganisms or cells, the culture medium is used as it is, or subjected to centrifugation to remove the microorganisms or cells. Thereafter, the resultant supernatant is subjected to conventional biochemical techniques used for isolating/purifying proteins. These techniques include ammonium sulfate precipitation, gel chromatography, ion exchange chromatography and affinity chromatography, and may be used independently or in an appropriate combination. Thus, the Del-1 partial fragment of the invention can be isolated/purified from the above-mentioned culture.

When an animal (experimental animal or domestic animal such as mouse, rat, rabbit, goat or bovine) or a plant is used as a transformant, they may require special breeding or culturing method such as ascetic environment or special feeds. If the transformant is one of the animals mentioned above, the Del-1 partial fragment of the invention may be isolated/purified from meat, eggs, hair, breastmilk, feces or the like of the transformant by using common biochemical techniques (such as ammonium sulfate precipitation, gel chromatography, ion exchange chromatography and affinity chromatography) independently or in combination.

When the transformant is a plant, the Del-1 partial fragment of the invention may be isolated/purified not only from leaves, flowers, fruits and roots of the transformant but also from the soil or water used for the cultivation, by using common biochemical techniques (such as ammonium sulfate precipitation, gel chromatography, ion exchange chromatography and affinity chromatography) independently or in combination.

In the present invention, synthesis of the Del-1 partial fragment by in vitro translation may be employed. Two methods may be available for the synthesis. One is a method using RNA as a template and the other is a method using DNA as a template (transcription/translation). As a template DNA, the above-described DNA having a promoter and a ribosome binding site upstream of the translation start point, or a DNA in which necessary elements for transcription (e.g., promoter) are integrated upstream of the translation start point may be used. As an in vitro translation system, a commercial system such as Expressway™ system (Invitrogen) or TNT system (registered trademark; Promega) may be used. After translation of the Del-1 partial fragment by an in vitro translation system, the fragment of interest can be isolated/purified by using the above-described biochemical methods independently or in combination.

4. Recovery of the Expression Product of the Gene of Interest

A cell system or an animal or plant expressing the Del-1 partial fragment and a molecule of interest may be used to recover the molecule of interest (i.e., expression product of the gene of interest) (for example, protein, antibody, peptide, natural or synthetic compound, other cell, or soluble molecule) by allowing expression of the gene of interest. Alternatively, the Del-1 partial fragment may be used directly.

The method of recovering a molecule of interest will be described below. First, a fusion protein in which a molecule of interest is bound to the Del-1 partial fragment is prepared. Briefly, a DNA encoding the molecule of interest and a DNA encoding the Del-1 partial fragment are linked, and the resultant DNA is linked to an appropriate vector. This vector is introduced into an appropriate host cell, which is then cultured to thereby produce the fusion protein in which the molecule of interest is linked. Methods of linking to the vector, introducing into the cell, culturing the transformant cell, and breeding of the transformant are as described in the preceding sections 2 and 3.

When the transformant cell is used, the entire region or a part of the Del-1 partial fragment in the fusion protein deposits onto extracellular matrix spreading on the culture dish. Therefore, even when the culture supernatant and cells have been removed after the cultivation, the fusion protein remains in the culture dish in a state of deposition onto extracellular matrix. Thus, it is possible to recover the molecule of interest by mechanically scraping the extracellular matrix onto which the fusion protein is depositing. Alternatively, it is possible to recover the molecule of interest alone by inserting in advance a recognition sequence of a specific enzyme (e.g., Factor Xa) between the nucleotide sequence of the molecule of interest and the nucleotide sequence of the Del-1 partial fragment and then using the enzyme. It is also possible to recover the molecule of interest into a solution by adding a negative regulation region to the Del-1 partial fragment.

Here, it is necessary to label the Del-1 partial fragment in order to identify and isolate the molecule of interest from the fusion protein in which the Del-1 partial fragment and the molecule of interest are linked. It is possible to label the Del-1 partial fragment with an enzyme such as alkaline phosphatase or horse radish peroxidase; or a reagent such as a fluorescent label containing fluoresceine isothiocyanate (FITC), phycocyanin or rhodamine.

Since the Del-1 partial fragment of the invention has deposition activity onto extracellular matrix, the partial fragment is applicable to binding assay, affinity chromatography, immunoprecipitation, Western blotting, and the like.

Identification of polypeptides of interest to be expressed which are capable of binding to the Del-1 partial fragment can also be performed by screening a peptide library with a recombinant Del-1 partial fragment.

Briefly, the above-described fusion protein which is labeled is incubated with a random peptide library to thereby bind the Del-1 partial fragment to peptides in the library. Subsequently, the library is washed to remove unbound polypeptides. To wells containing a substrate for alkaline phosphatase or peroxidase (e.g., 5-bromo4-chloro-3-indolylphosphate (BCIP) or 3,3'-diaminobenzidine (DAB)), peptides of the library are added and incubated for several minutes. Then, alkaline phosphatase or the like develops a color. Thus, molecules of interest can be easily identified and isolated.

In the case of the transformant being an animal or plant, when the above-described fusion protein is expressed in a specific site of the animal or plant, the Del-1 partial fragment of the invention deposits onto extracellular matrix to thereby concentrate the protein of interest in that tissue. Therefore, the molecule of interest can be efficiently recovered and used by directly eating the relevant agricultural or livestock product or by extracting biochemically.

5. Identification of Deposition Sites on Extracellular Matrix

As described in the preceding section 1, the Del-1 partial fragment of the invention has deposition activity onto extracellular matrix. By using a deposition marker, it is possible to observe visually the deposition site of the Del-1 partial fragment of the invention on extracellular matrix.

Therefore, the Del-1 partial fragment of the invention is useful as a reagent for identifying the deposition site on extracellular matrix and can be included in an extracellular matrix deposition site identification kit together with a marker, a color development substrate, an antibody to the marker, etc.

6. Immobilization of Biologically Active Substances at Specific Sites in the Living Body When a fusion protein composed of a molecule of interest and the Del-1 partial fragment of the invention is expressed in a specific tissue, the molecule of interest is immobilized at the specific site and does not migrate to other sites. As a result, the molecule of interest is concentrated at that site.

Therefore, the nucleotide sequence encoding the Del-1 partial fragment of the invention can be used, in combination with a promoter sequence specific to an appropriate cell, tissue or organ, as a vector for expressing a molecule of interest in a specific tissue and immobilizing, localizing and concentrating the molecule.

Further, as a result of staining with BCIP, it was found that extracellular alkaline phosphatase activity is present in extracellular matrix (Example 2).

This means that the partial fragment of Del-1 protein has much higher ability to deposit onto extracellular matrix than the full-length Del-1 protein, and has an effect of immobilizing other proteins such as alkaline phosphatase in extracellular matrix.

7. Modification of Artifacts with Biologically Active Substances

Figure 2:

It is possible to allow a biologically active substance to deposit onto an artifact without damaging its biological function, by culturing on the artifact E. coli or other cells producing a fusion protein composed of the biologically active substance and the Del-1 partial fragment of the invention. For example, the results of FIG. 2 show that a culture dish (an artifact) has been modified with alkaline phosphatase (a biologically active substance). This is applicable to modification of membranes for hemodialysis and artificial materials for implantation.

8. Regulation of Deposition Activity and Drug Delivery System

When linked to a molecule of interest, the Del-1 partial fragment of the invention is capable of allowing the molecule to deposit onto extracellular matrix. Further, it is possible to artificially regulate the deposition activity of the Del-1 partial fragment of the invention by using a positive regulation region and a negative regulation region. For example, it is possible to change the degree of deposition activity by the presence or absence of YB region or XC region as shown in FIG. 1, or by appropriately changing the lengths of these regions (see, for example, 4-8, 4-13, 4-1 and XY in FIG. 1). Specifically, a fragment comprising the active center region CY (SEQ ID NOS: 4 and 5) and the positive regulation region (SEQ ID NOS: 19 and 20), a fragment comprising the active center region CY (SEQ ID NOS: 4 and 5) and the negative regulation region (SEQ ID NOS: 21 and 22) or both of these fragments may be reacted with extracellular matrix for positive or negative regulation, to thereby obtain deposition activities of varied strengths, wherein all of these fragments are in the amino acid sequence as shown in SEQ ID NO: 2. Therefore, when the molecule of interest is a protein having a specific pharmacological effect, the fusion protein of the invention may be used as a drug delivery system (DDS). For example, a gene encoding a fusion protein composed of fragment 4-1 comprising the center region and the positive regulation region and an enzyme that converts a precursor of an anticancer agent into the anticancer agent is transferred into cancer tissues in advance. Subsequently, a large dose of the precursor is administered. Then, a higher drug concentration is achieved in cancer tissues than normal tissues. After the treatment, by introducing a gene encoding fragment CB (SEQ ID NOS: 13 and 14) comprising the negative regulation region, the gene product of the previously introduced gene is released into blood and becomes capable of removal by hemodialysis or the like.

EXAMPLES

Hereinbelow, the present invention will be described more specifically with reference to the following Examples. However, the present invention is not limited to these Examples.

Example 1

Preparation of Del-1 Partial Fragments

RNA was extracted from mouse embryos 9 to 12 days after fertilization using TRIzol (Invitrogen). Using the resultant RNA as a template, reverse transcription was performed to prepare cDNA. The nucleotide sequence from positions 697 to 2089 corresponding to the amino acid sequence as shown in SEQ ID NO: 2 with its signal peptide sequence deleted was amplified by PCR. A restriction enzyme recognition sequence was added at the 5' end of the primer so that the above nucleotide sequence can be inserted into a vector after PCR amplification. The nucleotide sequences of the primers are as described below.

(SEQ ID NO: 25)
Forward primer: AAA GAT CTAACC CGAACC CCT GTG AA (SEQ ID NO: 26)
Reverse primer: AAC TCG AGC ATT GTG GGA TGT GCG PCR was performed using a reaction solution with the following composition for 35 cycles at 94° C., 30 seconds; 62° C., 30 seconds; 72° C., 1 minute and 30 seconds.

| Composition of the reaction solution (in 50 μl): | |
|---|---|
| cDNA produced by a reverse transcriptase | 5 μl |
| Primers | 1 μM for each |
| dNTPs | 0.5 mM for each |
| Polymerase | 2 units |
| Buffer | 10 mM Tris-HCl (pH 8.3) |
| | 50 mM KCl |
| | 1.5 mM MgCl$_2$ |

The resultant PCR product was treated with restriction enzymes Bgl II and XhoI, and then ligated to plasmid pATtag-5 (Funakoshi). The thus prepared plasmid was digested with Xho I and then treated with Exonuclease III (Takara Bio) for 10 seconds to 2 minutes, to thereby prepare Del-1 partial fragments with varied lengths shown in FIG. 1 (4-8, 4-13, 4-14, 4-1, 4-11, 2-6, Del-1 minor, 1-1 and 2-3). Also, Del-1 partial fragments with varied lengths shown in FIG. 1 (CB, CY, YB, XY, XC, human XY, and AP only) and Del-1 partial fragments not shown in FIG. 1 (FB: positions 1576-2059 of the nucleotide sequence as shown in SEQ ID NO: 1; 4-15: SEQ ID NO: 8; and CE: SEQ ID NO: 16) were prepared by PCR.

Example 2

Deposition Activity of Del-1 Partial Fragments onto Extracellular Matrix (1) Of the partial fragments prepared in Example 1, 4-8, 4-13, 4-14, 4-1, 4-11, 2-6, Del-1 minor, 1-1 and 2-3 were ligated to plasmid pAPtag-5 (Funakoshi) and introduced into cos7 cells. Three days after the introduction, the culture supernatant, cells and extracellular matrix were collected. First, after collecting the culture supernatant, 0.05% EDTA-containing PBS was added to the culture dish and incubated. This operation allows cells to peel off from the bottom of the culture dish and to become collectable. As a result, the extracellular matrix is left on the bottom of the culture dish. Thus, alkaline phosphatase activities in these fractions were detected. As controls, samples of the wild-type, full-length Del-1 (AP4Del-1) and the medium alone were prepared, followed by detection of alkaline phosphatase activities therein. Alkaline phosphatase activity was determined as a ratio of the activity in extracellular matrix to the activity in culture supernatant (AP activity ratio; ECM/Medium) and shown in a graph at the right side of FIG. 1.

From FIG. 1, it can be seen that 4-1, 4-8, 4-14 and 4-13 have stronger activity than the wild-type Del-1 (Del-1 major); that 4-11 and 2-6 have lower activity than Del-1 major; and that Del-1 minor has little activity.

In order to examine the center region of deposition activity, CB (positions 1270-2058 of the nucleotide sequence as shown in SEQ ID NO: 1), CY, YB, XY, XC, human XY and AP only were expressed, and alkaline phosphatase activities therein were measured in the same manner as described above.

As a result, XY and human XY have higher alkaline phosphatase activity than the wild-type full-length Del-1, and CB and CY have some alkaline phosphatase activity. On the other hand, no alkaline phosphatase activity was recognized in XC and YB.

From these results, it was believed that the active center region is CY encoded by SEQ ID NO: 3 (a region spanning from positions 1270 to 1662 of the nucleotide sequence as shown in SEQ ID NO: 1) which corresponds to a region spanning from positions 218 to 348 of the amino acid sequence as shown in SEQ ID NO: 2.

XY, which consists of CY and XC ligated, has deposition activity about 10 times higher that that of CY (active center region) alone. XC alone has little deposition activity. Therefore, it was believed that XC is a positive regulation region for deposition activity which improves deposition activity onto extracellular matrix.

On the other hand, the deposition activity of CB, which consist of CY and YB ligated, is reduced to about 0.5 times the activity of the active center region CY alone. Therefore, it was believed that YB is a negative regulation region for deposition activity which decreases deposition activity onto extracellular matrix.

(2) Further, from the Del-1 partial fragments prepared in Example 1, Del-1 minor (positions 619-1271 of the nucleotide sequence as shown in SEQ ID NO: 1) or 4-1 was ligated to plasmid pAPtag-5 (Funakoshi) and introduced into cos7 cells. Three days after the introduction, the culture supernatant, cells and extracellular matrix were collected. First, after collecting the culture supernatant, 0.05% EDTA-containing PBS was added to the culture dish and incubated. This operation allows cells to peel off from the bottom of the culture dish and to become collectable. As a result, the extracellular matrix is left on the bottom of the culture dish. Thus, alkaline phosphatase activities in these fractions were detected.

The results are shown in FIG. 2. In FIG. 2, panels A to D show the results from those samples prepared using Del-1 minor; and panels E to H show the results from those samples prepared using 4-1. Panels A and E show the results of staining cells with an alkaline phosphatase substrate of deposition property (BCIP). Panels B and F show the results of staining the remaining extracellular matrix with BCIP after peeling cells off with 0.05% EDTA. Panels C and G show the results of color development in the remaining extracellular matrix by addition of a soluble alkaline phosphatase substrate (PNPP) thereto after peeling cells off with 0.05% EDTA. Panels D and H show the results of color development reaction by addition of PNPP to the cell culture medium (culture supernatant) in the same manner as in conventional methods.

Those sites stained purple are alkaline phosphatase activity sites, i.e., the deposition sites of 4-1 (E and F). From the results shown in E and F in FIG. 2, it is found that 4-1 deposited onto cells and extracellular matrix. On the other hand, Del-1 minor did not deposit either cells or extracellular matrix (A and B).

Likewise, extracellular matrix was stained yellow with the soluble substrate PNPP (G) when 4-1 was used, but extracellular matrix was not stained at all when Del-1 minor was used (C). Further, when PNPP was added to cell culture medium for color development reaction, the culture medium was stained yellow when Del-1 minor was used (D) but no color development was observed when 4-1 was used (H). Therefore, it has been found that 4-1 deposited onto extracellular matrix but Del-1 minor deposited little.

In the present invention, it is possible to measure the alkaline phosphatase activity in extracellular matrix with an absorptionmeter or the like by allowing the substrate of alkaline phosphatase to develop a color using soluble alkaline phosphatase as shown in G in FIG. 2.

Then, the inventor measured alkaline phosphatase activities in extracellular matrix and cell culture medium on the Del-1 partial fragment (4-1) and the full-length Del-1, and compared them. The results revealed that the Del-1 partial fragment (4-1) has 2.5-fold higher deposition activity onto extracellular matrix than the full-length Del-1.

(3) A truncated Del-1 gene sequence (XY) as shown in SEQ ID NO: 17 (one of the Del-1 partial fragments prepared in Example 1) was ligated to alkali phosphatase gene, and the resultant DNA (AP/XY) was introduced into mouse livers. As a control, mouse livers into which alkali phosphatase gene (AP) alone was introduced were prepared. Twenty-four hours after the gene transfer, plasma and hepatic tissues were taken from individual livers, followed by measurement of alkaline phosphatase activities.

Figure 3:
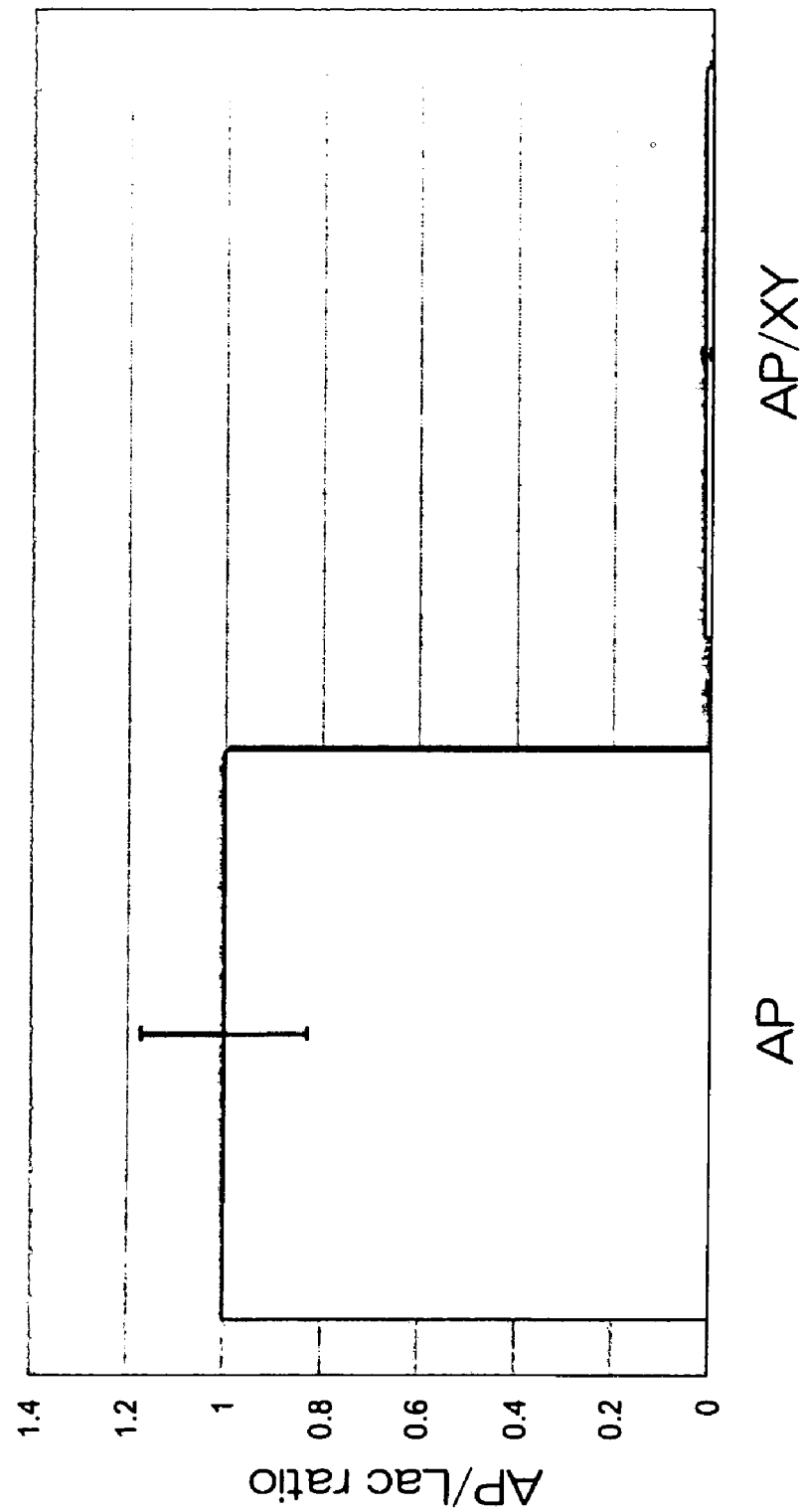
Figure 4:
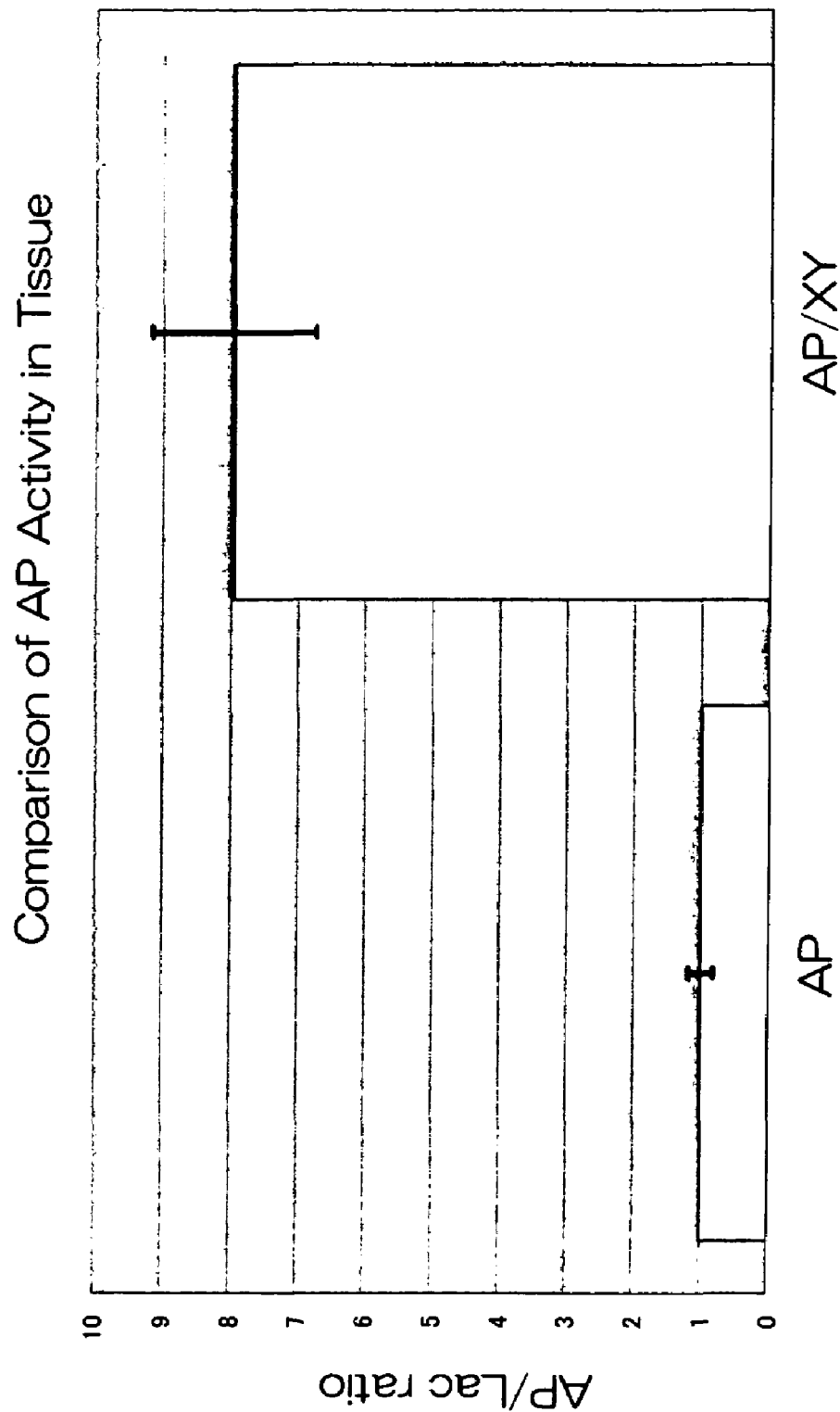

In the above-gene transfer, β-galactosidase gene was introduced simultaneously with the above-mentioned AP/XY or AP in order to standardize the efficiency of gene transfer. β-Galactosidase activity was also measured together with alkaline phosphatase activity. The quotient obtained by dividing the measured alkaline phosphatase activity by the value of β-galactosidase activity was taken as the measured value (AP/Lac ratio). Further, AP/Lac ratio in the plasma or hepatic tissue taken from livers of those mice into which the DNA composed of XY and alkaline phosphatase gene ligated (AP/XY) was introduced is shown in graphs, taking the corresponding AP/Lac ratio in control mouse into which alkaline phosphatase gene (AP) alone was introduced as "1". FIG. 3 shows AP/Lac ratios in the plasma taken from individual livers. FIG. 4 shows AP/Lac ratios in the hepatic tissues taken from individual livers.

With respect to AP/Lac ratio in hepatic tissues, hepatic tissues taken from AP/XY-introduced livers showed about 8-fold higher AP/Lac ratio than hepatic tissues taken from AP alone introduced livers (FIG. 4). On the other hand, with respect to AP/Lac ratio in plasma, AP activity was hardly detected in the plasma taken from AP/XY-introduced livers and, thus, the AP/Lac ratio was almost 0.

(4) Three cryosections were prepared from AP/XY-introduced mouse livers prepared in (3) (B, E and F). Similarly, three cryosections were prepared from AP alone introduced mouse livers (A, C and D).

Figure 5:
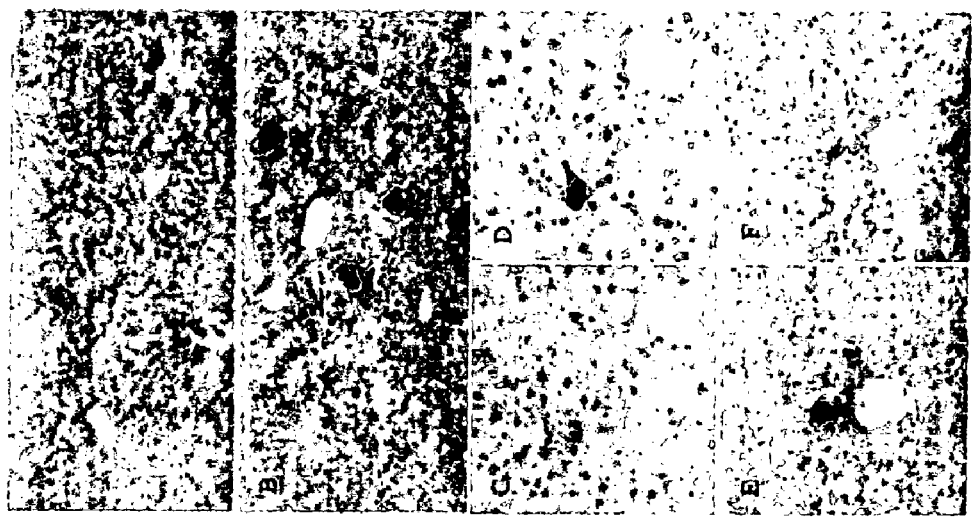

FIG. 5 shows the results of alkaline phosphatase staining (A, B, C and E) and β-galactosidase staining (D and F) on the cryosections of hepatic tissues taken from individual livers. A and B were observed at ×40 magnification, and C, D, E and F at ×200 magnification. Compared to AP (cryosections A), AP/XY (cryosections B) deposits remarkably. Cryosections C and D and cryosections E and F were serial sections, respectively, and stained with both alkaline phosphatase and β-galactosidase staining. AP (cryosections C and D) is also stained with β-galactosidase staining (cryosections D and F) in the same manner as seen in AP/XY (cryosections E and F). This indicates that there is no difference in gene transfer efficiency.

(5) Subsequently, the full-length Del-1 and the Del-1 partial fragment XY prepared in Example 1 were detected by Western blotting. Specifically, the three genes described below were prepared and introduced into cos7 cells.

(i) a DNA in which the full-length Del-1 gene sequence as shown in SEQ ID NO: 1 (Del-1 major) and alkaline phosphatase gene are ligated (AP/Del-1)

(ii) a DNA in which the truncated Del-1 gene sequence as shown in SEQ ID NO: 17 (XY) and alkaline phosphatase gene are ligated (AP/XY)

(iii) as a control, alkaline phosphatase gene alone (AP)-introduced cos7 cells were prepared; and cos7 cells without gene transfer (NC) were also prepared.

Subsequently, the above-described four types of cos7 cells were cultured individually for 72 hours. Then, the culture medium and extracellular matrix (ECM) were collected and subjected to Western blotting. As controls, laminin and albumin were used.

Figure 6:
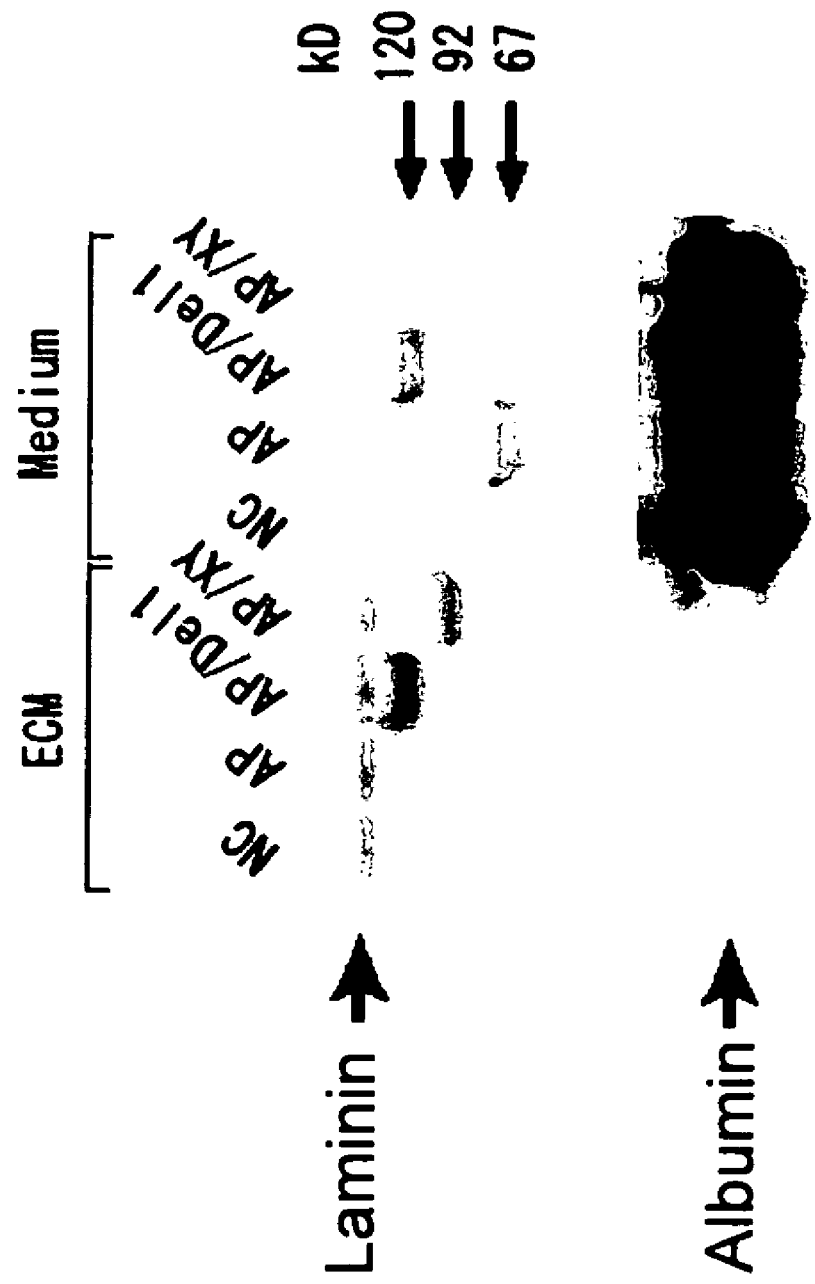

FIG. 6 is photographs showing the results of electrophoresis in the Western blotting. The upper photograph shows electrophoresis using laminin as a control. The lower photograph shows electrophoresis using albumin as a control.

According to FIG. 6, when AP alone introduced cos7 cells were used, the recombinant protein of alkaline phosphatase was not detected in extracellular matrix, as seen in the case of cos7 cells without gene transfer (NC). However, the recombinant protein was detected in the medium. On the other hand, when AP/Del-1 or AP/XY introduced cos7 cells were used, the recombinant protein of alkaline phosphatase was detected highly in extracellular matrix.

Example 3

Recovery of Molecules of Interest

This Example illustrates an example in which alkaline phosphatase is recovered as the expression product from a gene of interest. The recovery of alkaline phosphatase was confirmed by detecting the color development reaction of alkaline phosphatase with its substrate.

Briefly, a DNA in which alkaline phosphatase gene and a truncated Del-1 gene sequence (4-1) are ligated was introduced into cos7 cells. As controls, wild-type cos7 cells and alkaline phosphatase gene alone introduced cos7 cells were also prepared.

These cells were cultured for 3 days. Then, the cells were removed with 0.05% EDTA solution, and the extracellular matrix remaining on the bottom of the culture dish was recovered with a scraper. The thus recovered sample was centrifuged and the resultant supernatant was removed to thereby prepare pellet. Subsequently, the same operations as in Example 2 (FIG. 3, B and F) were performed, and BCIP (substrate of alkaline phosphatase) was added to the pellet for color development.

The results are shown in FIG. 7. In FIG. 7, panel (a) shows the results in wild-type cos7 cells; panel (b) shows the results in alkaline phosphatase gene alone introduced cos7 cells; and panel (c) shows the results in the fusion gene (4-1 partial fragment+alkaline phosphatase gene) introduced cos7 cells. As shown previously in FIG. 7, in sample (c) into which a Del-1 partial fragment (4-1) was introduced, the pellet was stained dark blue purple. This demonstrates that alkaline phosphatase was recovered into insoluble extracellular matrix through the Del-1 partial fragment (4-1). In contrast, color development was hardly observed in control cells, indicating that little alkaline phosphatase was recovered.

INDUSTRIAL APPLICABILITY

By using the Del-1 partial fragment of the present invention, it is possible to allow a molecule of interest to deposit onto extracellular matrix or artificial materials efficiently. The Del-1 partial fragment of the present invention is also useful in recovering or removing a molecule of interest by means of the above-mentioned deposition. According to the present invention, by using the Del-1 partial fragment, it is possible to allow a molecule of interest to deposit onto extracellular matrix to thereby prevent the flow out of the molecule into plasma highly. Thus, a fusion protein having the Del-1 partial fragment of the invention and the molecule of interest may be used as a drug delivery system with less side effect. Further, by regulating deposition activity with the Del-1 partial fragment of the invention, it is possible to highly control the degree of concentration at a specific site or localization of the molecule of interest. Thus, such a fusion protein may be used as an extremely highly functional drug delivery system.

The invention claimed is:

1. An isolated protein consisting of the amino acid sequence as shown in SEQ ID NO: 24.

2. A solution comprising the protein according to claim 1.

3. A fusion protein composed of the protein according to claim 1 linked to a molecule of interest to be expressed.

4. A drug delivery system comprising the fusion protein according to claim 3.

* * * * *

SEQUENCE LISTING

```
<160> NUMBER OF SEQ ID NOS: 26

<210> SEQ ID NO 1
<211> LENGTH: 2303
<212> TYPE: DNA
<213> ORGANISM: Mus musculus
<220> FEATURE:
<221> NAME/KEY: CDS
<222> LOCATION: (619)..(2061)

<400> SEQUENCE: 1
gaattccggt taactgagga caaagggtaa tgcagaagtg atatttgatt tccattctca      60
ttcccagtgg ccttgatatt taaactgatt cctgccacca ggtccttggg ccaccctgtc     120
cctgcgtctc atatttctgc atgctgcttt gtttgtatat agtgcgctcc tggcctcagg     180
ctcgctcccc tccagctctc gcttcattgt tctccaagtc agaagccccc gcatccgccg     240
cgcagcagcg tgagccgtag tcactgctgg ccgcttcgcc tgcgtgcgcg cacggaaatc     300
ggggagccag gaacccaagg agccgccgtc cgcccgctgt gcctctgcta gaccactcgc     360
agccccagcc tctctcaagc gcacccacct ccgcgcaccc cagctcaggc gaagctggag     420
tgagggtgaa tcacccttc tctagggcca ccactctttt atcgcccttc caagatttg      480 agaagcgctg cgggaggaaa gacgtcctct tgatctctga cagggcgggg tttactgctg     540
tcctgcaggc gcgcctcgcc tactgtgccc tccgctacga ccccggacca gcccaggtca     600
```

```
                                        -continued cgtccgtgag aagggatc atg aag cac ttg gta gca gcc tgg ctt ttg gtt        651
                   Met Lys His Leu Val Ala Ala Trp Leu Leu Val
                    1               5                  10 gga ctc agc ctc ggg gtg ccc cag ttc ggc aaa ggt gac att tgc aac        699
Gly Leu Ser Leu Gly Val Pro Gln Phe Gly Lys Gly Asp Ile Cys Asn
            15                  20                  25 ccg aac ccc tgt gaa aat ggt ggc atc tgt ctg tca gga ctg gct gat        747
Pro Asn Pro Cys Glu Asn Gly Gly Ile Cys Leu Ser Gly Leu Ala Asp
        30                  35                  40 gat tcc ttt tcc tgt gag tgt cca gaa ggc ttc gca ggt ccg aac tgc        795
Asp Ser Phe Ser Cys Glu Cys Pro Glu Gly Phe Ala Gly Pro Asn Cys
    45                  50                  55 tct agt gtt gtg gag gtt gca tca gat gaa gaa aag cct act tca gca        843
Ser Ser Val Val Glu Val Ala Ser Asp Glu Glu Lys Pro Thr Ser Ala
60                  65                  70                  75 ggt ccc tgc atc cct aac cca tgc cat aac gga gga acc tgt gag ata        891
Gly Pro Cys Ile Pro Asn Pro Cys His Asn Gly Gly Thr Cys Glu Ile
                80                  85                  90 agc gaa gcc tat cga gga gac aca ttc ata ggc tat gtt tgt aaa tgt        939
Ser Glu Ala Tyr Arg Gly Asp Thr Phe Ile Gly Tyr Val Cys Lys Cys
            95                  100                 105 cct cgg gga ttt aat ggg att cac tgt cag cac aat ata aat gaa tgt        987
Pro Arg Gly Phe Asn Gly Ile His Cys Gln His Asn Ile Asn Glu Cys
        110                 115                 120 gaa gct gag cct tgc aga aat ggc gga ata tgt acc gac ctt gtt gct       1035
Glu Ala Glu Pro Cys Arg Asn Gly Gly Ile Cys Thr Asp Leu Val Ala
    125                 130                 135 aac tac tct tgt gaa tgc cca gga gaa ttt atg gga cga aat tgt caa       1083
Asn Tyr Ser Cys Glu Cys Pro Gly Glu Phe Met Gly Arg Asn Cys Gln
140                 145                 150                 155 tat aaa tgc tct ggg cca ttg gga atc gaa ggt ggg atc ata tct aat       1131
Tyr Lys Cys Ser Gly Pro Leu Gly Ile Glu Gly Gly Ile Ile Ser Asn
                160                 165                 170 cag caa atc aca gct tca tct act cac cga gct ctt ttt gga ctc cgg       1179
Gln Gln Ile Thr Ala Ser Ser Thr His Arg Ala Leu Phe Gly Leu Arg
            175                 180                 185 aag tgg tat ccc tac tat gct cga ctt aat aag aag ggc ctt ata aat       1227
Lys Trp Tyr Pro Tyr Tyr Ala Arg Leu Asn Lys Lys Gly Leu Ile Asn
        190                 195                 200 gcc tgg aca gct gct gaa aat gac aga tgg cca tgg att cag ata aat       1275
Ala Trp Thr Ala Ala Glu Asn Asp Arg Trp Pro Trp Ile Gln Ile Asn
    205                 210                 215 ttg caa aga aaa atg aga gtc act ggt gtt att acc caa gga gca aaa       1323
Leu Gln Arg Lys Met Arg Val Thr Gly Val Ile Thr Gln Gly Ala Lys
220                 225                 230                 235 agg att gga agc cca gag tac ata aaa tcc tac aaa att gcc tac agc       1371
Arg Ile Gly Ser Pro Glu Tyr Ile Lys Ser Tyr Lys Ile Ala Tyr Ser
                240                 245                 250 aat gac ggg aag acc tgg gca atg tac aaa gta aaa ggc acc aat gaa       1419
Asn Asp Gly Lys Thr Trp Ala Met Tyr Lys Val Lys Gly Thr Asn Glu
            255                 260                 265 gag atg gtc ttt cgt gga aat gtt gat aac aac aca cca tat gct aat       1467
Glu Met Val Phe Arg Gly Asn Val Asp Asn Asn Thr Pro Tyr Ala Asn
        270                 275                 280 tct ttc aca ccc cca atc aaa gct cag tat gta aga ctc tac ccc caa       1515
Ser Phe Thr Pro Pro Ile Lys Ala Gln Tyr Val Arg Leu Tyr Pro Gln
    285                 290                 295 att tgt cga agg cat tgt act tta aga atg gaa ctt ctt ggc tgt gag       1563
Ile Cys Arg Arg His Cys Thr Leu Arg Met Glu Leu Leu Gly Cys Glu
300                 305                 310                 315
```

```
ctc tca ggc tgt tca gaa cct ttg ggg atg aaa tca ggg cat ata caa    1611
Leu Ser Gly Cys Ser Glu Pro Leu Gly Met Lys Ser Gly His Ile Gln
            320                 325                 330 gac tac cag atc act gcc tcc agc gtc ttc aga aca ctc aac atg gac    1659
Asp Tyr Gln Ile Thr Ala Ser Ser Val Phe Arg Thr Leu Asn Met Asp
                335                 340                 345 atg ttt act tgg gaa cca agg aaa gcc agg ctg gac aag caa ggc aaa    1707
Met Phe Thr Trp Glu Pro Arg Lys Ala Arg Leu Asp Lys Gln Gly Lys
        350                 355                 360 gta aat gcc tgg act tcc ggc cat aac gac cag tca caa tgg tta cag    1755
Val Asn Ala Trp Thr Ser Gly His Asn Asp Gln Ser Gln Trp Leu Gln
365                 370                 375 gtt gat ctt ctt gtc cct act aag gtg aca ggc att att aca caa gga    1803
Val Asp Leu Leu Val Pro Thr Lys Val Thr Gly Ile Ile Thr Gln Gly
380                 385                 390                 395 gct aaa gat ttt ggt cac gtg cag ttt gtt ggg tca tac aaa cta gct    1851
Ala Lys Asp Phe Gly His Val Gln Phe Val Gly Ser Tyr Lys Leu Ala
                400                 405                 410 tac agc aat gat gga gaa cac tgg atg gtg cac cag gat gaa aaa cag    1899
Tyr Ser Asn Asp Gly Glu His Trp Met Val His Gln Asp Glu Lys Gln
            415                 420                 425 agg aaa gac aag gtt ttt caa ggc aat ttt gac aat gac act cac agg    1947
Arg Lys Asp Lys Val Phe Gln Gly Asn Phe Asp Asn Asp Thr His Arg
        430                 435                 440 aaa aat gtc atc gac cct ccc atc tat gca cga ttc ata aga atc ctt    1995
Lys Asn Val Ile Asp Pro Pro Ile Tyr Ala Arg Phe Ile Arg Ile Leu
    445                 450                 455 cct tgg tcc tgg tat gga agg atc act ctg cgg tca gag ctg ctg ggc    2043
Pro Trp Ser Trp Tyr Gly Arg Ile Thr Leu Arg Ser Glu Leu Leu Gly
460                 465                 470                 475 tgc gca gag gag gaa tga agtgcggggc cgcacatccc acaatgcttt           2091
Cys Ala Glu Glu Glu
                480 tctttatttt cctataagta tctccacgaa atgaactgtg tgaagctgat ggaaactgca    2151 tttgttttt tcaaagtgtt caaattatgg taggctactg actgtctttt taggagttct    2211 aagcttgcct ttttaataat ttaatttggt ttcctttgct caactctctt atgtaatatc    2271 acactgtctg tgagttactc ttcttgttct ct                                  2303

<210> SEQ ID NO 2
<211> LENGTH: 480
<212> TYPE: PRT
<213> ORGANISM: Mus musculus

<400> SEQUENCE: 2

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
                20                  25                  30

Asn Gly Gly Ile Cys Leu Ser Gly Leu Ala Asp Asp Ser Phe Ser Cys
            35                  40                  45

Glu Cys Pro Glu Gly Phe Ala Gly Pro Asn Cys Ser Ser Val Val Glu
        50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95
```

```
Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
            115                 120                 125

Arg Asn Gly Gly Ile Cys Thr Asp Leu Val Ala Asn Tyr Ser Cys Glu
130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
                165                 170                 175

Ser Ser Thr His Arg Ala Leu Phe Gly Leu Arg Lys Trp Tyr Pro Tyr
            180                 185                 190

Tyr Ala Arg Leu Asn Lys Lys Gly Leu Ile Asn Ala Trp Thr Ala Ala
            195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Glu Met Val Phe Arg
            260                 265                 270

Gly Asn Val Asp Asn Asn Thr Pro Tyr Ala Asn Ser Phe Thr Pro Pro
            275                 280                 285

Ile Lys Ala Gln Tyr Val Arg Leu Tyr Pro Gln Ile Cys Arg Arg His
    290                 295                 300

Cys Thr Leu Arg Met Glu Leu Leu Gly Cys Glu Leu Ser Gly Cys Ser
305                 310                 315                 320

Glu Pro Leu Gly Met Lys Ser Gly His Ile Gln Asp Tyr Gln Ile Thr
                325                 330                 335

Ala Ser Ser Val Phe Arg Thr Leu Asn Met Asp Met Phe Thr Trp Glu
            340                 345                 350

Pro Arg Lys Ala Arg Leu Asp Lys Gln Gly Lys Val Asn Ala Trp Thr
            355                 360                 365

Ser Gly His Asn Asp Gln Ser Gln Trp Leu Gln Val Asp Leu Leu Val
    370                 375                 380

Pro Thr Lys Val Thr Gly Ile Ile Thr Gln Gly Ala Lys Asp Phe Gly
385                 390                 395                 400

His Val Gln Phe Val Gly Ser Tyr Lys Leu Ala Tyr Ser Asn Asp Gly
                405                 410                 415

Glu His Trp Met Val His Gln Asp Glu Lys Gln Arg Lys Asp Lys Val
            420                 425                 430

Phe Gln Gly Asn Phe Asp Asn Asp Thr His Arg Lys Asn Val Ile Asp
            435                 440                 445

Pro Pro Ile Tyr Ala Arg Phe Ile Arg Ile Leu Pro Trp Ser Trp Tyr
    450                 455                 460

Gly Arg Ile Thr Leu Arg Ser Glu Leu Leu Gly Cys Ala Glu Glu
465                 470                 475                 480

<210> SEQ ID NO 3
<211> LENGTH: 393
<212> TYPE: DNA
<213> ORGANISM: Mus musculus
```

```
<220> FEATURE:
<221> NAME/KEY: CDS
<222> LOCATION: (1)..(393)

<400> SEQUENCE: 3 ata aat ttg caa aga aaa atg aga gtc act ggt gtt att acc caa gga      48
Ile Asn Leu Gln Arg Lys Met Arg Val Thr Gly Val Ile Thr Gln Gly
1               5                   10                  15 gca aaa agg att gga agc cca gag tac ata aaa tcc tac aaa att gcc      96
Ala Lys Arg Ile Gly Ser Pro Glu Tyr Ile Lys Ser Tyr Lys Ile Ala
            20                  25                  30 tac agc aat gac ggg aag acc tgg gca atg tac aaa gta aaa ggc acc     144
Tyr Ser Asn Asp Gly Lys Thr Trp Ala Met Tyr Lys Val Lys Gly Thr
        35                  40                  45 aat gaa gag atg gtc ttt cgt gga aat gtt gat aac aac aca cca tat     192
Asn Glu Glu Met Val Phe Arg Gly Asn Val Asp Asn Asn Thr Pro Tyr
    50                  55                  60 gct aat tct ttc aca ccc cca atc aaa gct cag tat gta aga ctc tac     240
Ala Asn Ser Phe Thr Pro Pro Ile Lys Ala Gln Tyr Val Arg Leu Tyr
65                  70                  75                  80 ccc caa att tgt cga agg cat tgt act tta aga atg gaa ctt ctt ggc     288
Pro Gln Ile Cys Arg Arg His Cys Thr Leu Arg Met Glu Leu Leu Gly
                85                  90                  95 tgt gag ctc tca ggc tgt tca gaa cct ttg ggg atg aaa tca ggg cat     336
Cys Glu Leu Ser Gly Cys Ser Glu Pro Leu Gly Met Lys Ser Gly His
            100                 105                 110 ata caa gac tac cag atc act gcc tcc agc gtc ttc aga aca ctc aac     384
Ile Gln Asp Tyr Gln Ile Thr Ala Ser Ser Val Phe Arg Thr Leu Asn
        115                 120                 125 atg gac atg                                                          393
Met Asp Met
    130

<210> SEQ ID NO 4
<211> LENGTH: 131
<212> TYPE: PRT
<213> ORGANISM: Mus musculus

<400> SEQUENCE: 4

Ile Asn Leu Gln Arg Lys Met Arg Val Thr Gly Val Ile Thr Gln Gly
1               5                   10                  15

Ala Lys Arg Ile Gly Ser Pro Glu Tyr Ile Lys Ser Tyr Lys Ile Ala
            20                  25                  30

Tyr Ser Asn Asp Gly Lys Thr Trp Ala Met Tyr Lys Val Lys Gly Thr
        35                  40                  45

Asn Glu Glu Met Val Phe Arg Gly Asn Val Asp Asn Asn Thr Pro Tyr
    50                  55                  60

Ala Asn Ser Phe Thr Pro Pro Ile Lys Ala Gln Tyr Val Arg Leu Tyr
65                  70                  75                  80

Pro Gln Ile Cys Arg Arg His Cys Thr Leu Arg Met Glu Leu Leu Gly
                85                  90                  95

Cys Glu Leu Ser Gly Cys Ser Glu Pro Leu Gly Met Lys Ser Gly His
            100                 105                 110

Ile Gln Asp Tyr Gln Ile Thr Ala Ser Ser Val Phe Arg Thr Leu Asn
        115                 120                 125

Met Asp Met
    130
```

<210> SEQ ID NO 5
<211> LENGTH: 1044
<212> TYPE: DNA
<213> ORGANISM: Mus musculus
<220> FEATURE:
<221> NAME/KEY: CDS
<222> LOCATION: (1)..(1044)

<400> SEQUENCE: 5

```
atg aag cac ttg gta gca gcc tgg ctt ttg gtt gga ctc agc ctc ggg      48
Met Lys His Leu Val Ala Ala Trp Leu Leu Val Gly Leu Ser Leu Gly
1               5                   10                  15 gtg ccc cag ttc ggc aaa ggt gac att tgc aac ccg aac ccc tgt gaa      96
Val Pro Gln Phe Gly Lys Gly Asp Ile Cys Asn Pro Asn Pro Cys Glu
            20                  25                  30 aat ggt ggc atc tgt ctg tca gga ctg gct gat gat tcc ttt tcc tgt     144
Asn Gly Gly Ile Cys Leu Ser Gly Leu Ala Asp Asp Ser Phe Ser Cys
        35                  40                  45 gag tgt cca gaa ggc ttc gca ggt ccg aac tgc tct agt gtt gtg gag     192
Glu Cys Pro Glu Gly Phe Ala Gly Pro Asn Cys Ser Ser Val Val Glu
    50                  55                  60 gtt gca tca gat gaa gaa aag cct act tca gca ggt ccc tgc atc cct     240
Val Ala Ser Asp Glu Glu Lys Pro Thr Ser Ala Gly Pro Cys Ile Pro
65                  70                  75                  80 aac cca tgc cat aac gga gga acc tgt gag ata agc gaa gcc tat cga     288
Asn Pro Cys His Asn Gly Gly Thr Cys Glu Ile Ser Glu Ala Tyr Arg
                85                  90                  95 gga gac aca ttc ata ggc tat gtt tgt aaa tgt cct cgg gga ttt aat     336
Gly Asp Thr Phe Ile Gly Tyr Val Cys Lys Cys Pro Arg Gly Phe Asn
            100                 105                 110 ggg att cac tgt cag cac aat ata aat gaa tgt gaa gct gag cct tgc     384
Gly Ile His Cys Gln His Asn Ile Asn Glu Cys Glu Ala Glu Pro Cys
        115                 120                 125 aga aat ggc gga ata tgt acc gac ctt gtt gct aac tac tct tgt gaa     432
Arg Asn Gly Gly Ile Cys Thr Asp Leu Val Ala Asn Tyr Ser Cys Glu
    130                 135                 140 tgc cca gga gaa ttt atg gga cga aat tgt caa tat aaa tgc tct ggg     480
Cys Pro Gly Glu Phe Met Gly Arg Asn Cys Gln Tyr Lys Cys Ser Gly
145                 150                 155                 160 cca ttg gga atc gaa ggt ggg atc ata tct aat cag caa atc aca gct     528
Pro Leu Gly Ile Glu Gly Gly Ile Ile Ser Asn Gln Gln Ile Thr Ala
                165                 170                 175 tca tct act cac cga gct ctt ttt gga ctc cgg aag tgg tat ccc tac     576
Ser Ser Thr His Arg Ala Leu Phe Gly Leu Arg Lys Trp Tyr Pro Tyr
            180                 185                 190 tat gct cga ctt aat aag aag ggc ctt ata aat gcc tgg aca gct gct     624
Tyr Ala Arg Leu Asn Lys Lys Gly Leu Ile Asn Ala Trp Thr Ala Ala
        195                 200                 205 gaa aat gac aga tgg cca tgg att cag ata aat ttg caa aga aaa atg     672
Glu Asn Asp Arg Trp Pro Trp Ile Gln Ile Asn Leu Gln Arg Lys Met
    210                 215                 220 aga gtc act ggt gtt att acc caa gga gca aaa agg att gga agc cca     720
Arg Val Thr Gly Val Ile Thr Gln Gly Ala Lys Arg Ile Gly Ser Pro
225                 230                 235                 240 gag tac ata aaa tcc tac aaa att gcc tac agc aat gac ggg aag acc     768
Glu Tyr Ile Lys Ser Tyr Lys Ile Ala Tyr Ser Asn Asp Gly Lys Thr
                245                 250                 255 tgg gca atg tac aaa gta aaa ggc acc aat gaa gag atg gtc ttt cgt     816
Trp Ala Met Tyr Lys Val Lys Gly Thr Asn Glu Glu Met Val Phe Arg
            260                 265                 270
```

```
gga aat gtt gat aac aac aca cca tat gct aat tct ttc aca ccc cca        864
Gly Asn Val Asp Asn Asn Thr Pro Tyr Ala Asn Ser Phe Thr Pro Pro
            275                 280                 285 atc aaa gct cag tat gta aga ctc tac ccc caa att tgt cga agg cat        912
Ile Lys Ala Gln Tyr Val Arg Leu Tyr Pro Gln Ile Cys Arg Arg His
    290                 295                 300 tgt act tta aga atg gaa ctt ctt ggc tgt gag ctc tca ggc tgt tca        960
Cys Thr Leu Arg Met Glu Leu Leu Gly Cys Glu Leu Ser Gly Cys Ser
305                 310                 315                 320 gaa cct ttg ggg atg aaa tca ggg cat ata caa gac tac cag atc act       1008
Glu Pro Leu Gly Met Lys Ser Gly His Ile Gln Asp Tyr Gln Ile Thr
                325                 330                 335 gcc tcc agc gtc ttc aga aca ctc aac atg gac atg                       1044
Ala Ser Ser Val Phe Arg Thr Leu Asn Met Asp Met
            340                 345
```

<210> SEQ ID NO 6
<211> LENGTH: 348
<212> TYPE: PRT
<213> ORGANISM: Mus musculus

<400> SEQUENCE: 6

```
Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
                165                 170                 175

Ser Ser Thr His Arg Ala Leu Phe Gly Leu Arg Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Glu Met Val Phe Arg
            260                 265                 270
```

```
                Gly Asn Val Asp Asn Asn Thr Pro Tyr Ala Asn Ser Phe Thr Pro Pro
                            275                 280                 285

Ile Lys Ala Gln Tyr Val Arg Leu Tyr Pro Gln Ile Cys Arg Arg His
                    290                 295                 300

Cys Thr Leu Arg Met Glu Leu Leu Gly Cys Glu Leu Ser Gly Cys Ser
                305                 310                 315                 320

Glu Pro Leu Gly Met Lys Ser Gly His Ile Gln Asp Tyr Gln Ile Thr
                                325                 330                 335

Ala Ser Ser Val Phe Arg Thr Leu Asn Met Asp Met
                            340                 345

<210> SEQ ID NO 7
<211> LENGTH: 1095
<212> TYPE: DNA
<213> ORGANISM: Mus musculus
<220> FEATURE:
<221> NAME/KEY: CDS
<222> LOCATION: (1)..(1095)

<400> SEQUENCE: 7
```

| | | |
|---|---|---|
| atg aag cac ttg gta gca gcc tgg ctt ttg gtt gga ctc agc ctc ggg<br>Met Lys His Leu Val Ala Ala Trp Leu Leu Val Gly Leu Ser Leu Gly<br>1               5                   10                  15 | 48 |
| gtg ccc cag ttc ggc aaa ggt gac att tgc aac ccg aac ccc tgt gaa<br>Val Pro Gln Phe Gly Lys Gly Asp Ile Cys Asn Pro Asn Pro Cys Glu<br>            20                  25                  30 | 96 |
| aat ggt ggc atc tgt ctg tca gga ctg gct gat gat tcc ttt tcc tgt<br>Asn Gly Gly Ile Cys Leu Ser Gly Leu Ala Asp Asp Ser Phe Ser Cys<br>        35                  40                  45 | 144 |
| gag tgt cca gaa ggc ttc gca ggt ccg aac tgc tct agt gtt gtg gag<br>Glu Cys Pro Glu Gly Phe Ala Gly Pro Asn Cys Ser Ser Val Val Glu<br>    50                  55                  60 | 192 |
| gtt gca tca gat gaa gaa aag cct act tca gca ggt ccc tgc atc cct<br>Val Ala Ser Asp Glu Glu Lys Pro Thr Ser Ala Gly Pro Cys Ile Pro<br>65                  70                  75                  80 | 240 |
| aac cca tgc cat aac gga gga acc tgt gag ata agc gaa gcc tat cga<br>Asn Pro Cys His Asn Gly Gly Thr Cys Glu Ile Ser Glu Ala Tyr Arg<br>                85                  90                  95 | 288 |
| gga gac aca ttc ata ggc tat gtt tgt aaa tgt cct cgg gga ttt aat<br>Gly Asp Thr Phe Ile Gly Tyr Val Cys Lys Cys Pro Arg Gly Phe Asn<br>            100                 105                 110 | 336 |
| ggg att cac tgt cag cac aat ata aat gaa tgt gaa gct gag cct tgc<br>Gly Ile His Cys Gln His Asn Ile Asn Glu Cys Glu Ala Glu Pro Cys<br>        115                 120                 125 | 384 |
| aga aat ggc gga ata tgt acc gac ctt gtt gct aac tac tct tgt gaa<br>Arg Asn Gly Gly Ile Cys Thr Asp Leu Val Ala Asn Tyr Ser Cys Glu<br>    130                 135                 140 | 432 |
| tgc cca gga gaa ttt atg gga cga aat tgt caa tat aaa tgc tct ggg<br>Cys Pro Gly Glu Phe Met Gly Arg Asn Cys Gln Tyr Lys Cys Ser Gly<br>145                 150                 155                 160 | 480 |
| cca ttg gga atc gaa ggt ggg atc ata tct aat cag caa atc aca gct<br>Pro Leu Gly Ile Glu Gly Gly Ile Ile Ser Asn Gln Gln Ile Thr Ala<br>                165                 170                 175 | 528 |
| tca tct act cac cga gct ctt ttt gga ctc cgg aag tgg tat ccc tac<br>Ser Ser Thr His Arg Ala Leu Phe Gly Leu Arg Lys Trp Tyr Pro Tyr<br>            180                 185                 190 | 576 |
| tat gct cga ctt aat aag aag ggc ctt ata aat gcc tgg aca gct gct<br>Tyr Ala Arg Leu Asn Lys Lys Gly Leu Ile Asn Ala Trp Thr Ala Ala<br>        195                 200                 205 | 624 |

```
gaa aat gac aga tgg cca tgg att cag ata aat ttg caa aga aaa atg       672
Glu Asn Asp Arg Trp Pro Trp Ile Gln Ile Asn Leu Gln Arg Lys Met
210             215                 220 aga gtc act ggt gtt att acc caa gga gca aaa agg att gga agc cca       720
Arg Val Thr Gly Val Ile Thr Gln Gly Ala Lys Arg Ile Gly Ser Pro
225             230                 235                 240 gag tac ata aaa tcc tac aaa att gcc tac agc aat gac ggg aag acc       768
Glu Tyr Ile Lys Ser Tyr Lys Ile Ala Tyr Ser Asn Asp Gly Lys Thr
            245                 250                 255 tgg gca atg tac aaa gta aaa ggc acc aat gaa gag atg gtc ttt cgt       816
Trp Ala Met Tyr Lys Val Lys Gly Thr Asn Glu Glu Met Val Phe Arg
        260                 265                 270 gga aat gtt gat aac aac aca cca tat gct aat tct ttc aca ccc cca       864
Gly Asn Val Asp Asn Asn Thr Pro Tyr Ala Asn Ser Phe Thr Pro Pro
    275                 280                 285 atc aaa gct cag tat gta aga ctc tac ccc caa att tgt cga agg cat       912
Ile Lys Ala Gln Tyr Val Arg Leu Tyr Pro Gln Ile Cys Arg Arg His
290                 295                 300 tgt act tta aga atg gaa ctt ctt ggc tgt gag ctc tca ggc tgt tca       960
Cys Thr Leu Arg Met Glu Leu Leu Gly Cys Glu Leu Ser Gly Cys Ser
305             310                 315                 320 gaa cct ttg ggg atg aaa tca ggg cat ata caa gac tac cag atc act      1008
Glu Pro Leu Gly Met Lys Ser Gly His Ile Gln Asp Tyr Gln Ile Thr
            325                 330                 335 gcc tcc agc gtc ttc aga aca ctc aac atg gac atg ttt act tgg gaa      1056
Ala Ser Ser Val Phe Arg Thr Leu Asn Met Asp Met Phe Thr Trp Glu
        340                 345                 350 cca agg aaa gcc agg ctg gac aag caa ggc aaa gta aat                  1095
Pro Arg Lys Ala Arg Leu Asp Lys Gln Gly Lys Val Asn
    355                 360                 365

<210> SEQ ID NO 8
<211> LENGTH: 365
<212> TYPE: PRT
<213> ORGANISM: Mus musculus

<400> SEQUENCE: 8

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160
```

```
Pro Leu Gly Ile Glu Gly Gly Ile Ile Ser Asn Gln Gln Ile Thr Ala
            165                 170                 175

Ser Ser Thr His Arg Ala Leu Phe Gly Leu Arg Lys Trp Tyr Pro Tyr
        180                 185                 190

Tyr Ala Arg Leu Asn Lys Lys Gly Leu Ile Asn Ala Trp Thr Ala Ala
    195                 200                 205

Glu Asn Asp Arg Trp Pro Trp Ile Gln Ile Asn Leu Gln Arg Lys Met
210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Glu Met Val Phe Arg
            260                 265                 270

Gly Asn Val Asp Asn Asn Thr Pro Tyr Ala Asn Ser Phe Thr Pro Pro
        275                 280                 285

Ile Lys Ala Gln Tyr Val Arg Leu Tyr Pro Gln Ile Cys Arg Arg His
    290                 295                 300

Cys Thr Leu Arg Met Glu Leu Leu Gly Cys Glu Leu Ser Gly Cys Ser
305                 310                 315                 320

Glu Pro Leu Gly Met Lys Ser Gly His Ile Gln Asp Tyr Gln Ile Thr
                325                 330                 335

Ala Ser Ser Val Phe Arg Thr Leu Asn Met Asp Met Phe Thr Trp Glu
            340                 345                 350

Pro Arg Lys Ala Arg Leu Asp Lys Gln Gly Lys Val Asn
        355                 360                 365

<210> SEQ ID NO 9
<211> LENGTH: 1104
<212> TYPE: DNA
<213> ORGANISM: Mus musculus
<220> FEATURE:
<221> NAME/KEY: CDS
<222> LOCATION: (1)..(1104)

<400> SEQUENCE: 9 atg aag cac ttg gta gca gcc tgg ctt ttg gtt gga ctc agc ctc ggg      48
Met Lys His Leu Val Ala Ala Trp Leu Leu Val Gly Leu Ser Leu Gly
1               5                   10                  15 gtg ccc cag ttc ggc aaa ggt gac att tgc aac ccg aac ccc tgt gaa      96
Val Pro Gln Phe Gly Lys Gly Asp Ile Cys Asn Pro Asn Pro Cys Glu
            20                  25                  30 aat ggt ggc atc tgt ctg tca gga ctg gct gat gat tcc ttt tcc tgt     144
Asn Gly Gly Ile Cys Leu Ser Gly Leu Ala Asp Asp Ser Phe Ser Cys
        35                  40                  45 gag tgt cca gaa ggc ttc gca ggt ccg aac tgc tct agt gtt gtg gag     192
Glu Cys Pro Glu Gly Phe Ala Gly Pro Asn Cys Ser Ser Val Val Glu
50                  55                  60 gtt gca tca gat gaa gaa aag cct act tca gca ggt ccc tgc atc cct     240
Val Ala Ser Asp Glu Glu Lys Pro Thr Ser Ala Gly Pro Cys Ile Pro
65                  70                  75                  80 aac cca tgc cat aac gga gga acc tgt gag ata agc gaa gcc tat cga     288
Asn Pro Cys His Asn Gly Gly Thr Cys Glu Ile Ser Glu Ala Tyr Arg
                85                  90                  95 gga gac aca ttc ata ggc tat gtt tgt aaa tgt cct cgg gga ttt aat     336
Gly Asp Thr Phe Ile Gly Tyr Val Cys Lys Cys Pro Arg Gly Phe Asn
            100                 105                 110
```

| | | |
|---|---|---|
| ggg att cac tgt cag cac aat ata aat gaa tgt gaa gct gag cct tgc<br>Gly Ile His Cys Gln His Asn Ile Asn Glu Cys Glu Ala Glu Pro Cys<br>115                              120                        125 | 384 |
| aga aat ggc gga ata tgt acc gac ctt gtt gct aac tac tct tgt gaa<br>Arg Asn Gly Gly Ile Cys Thr Asp Leu Val Ala Asn Tyr Ser Cys Glu<br>130                              135                        140 | 432 |
| tgc cca gga gaa ttt atg gga cga aat tgt caa tat aaa tgc tct ggg<br>Cys Pro Gly Glu Phe Met Gly Arg Asn Cys Gln Tyr Lys Cys Ser Gly<br>145                              150                        155                        160 | 480 |
| cca ttg gga atc gaa ggt ggg atc ata tct aat cag caa atc aca gct<br>Pro Leu Gly Ile Glu Gly Gly Ile Ile Ser Asn Gln Gln Ile Thr Ala<br>                        165                        170                        175 | 528 |
| tca tct act cac cga gct ctt ttt gga ctc cgg aag tgg tat ccc tac<br>Ser Ser Thr His Arg Ala Leu Phe Gly Leu Arg Lys Trp Tyr Pro Tyr<br>                        180                        185                        190 | 576 |
| tat gct cga ctt aat aag aag ggc ctt ata aat gcc tgg aca gct gct<br>Tyr Ala Arg Leu Asn Lys Lys Gly Leu Ile Asn Ala Trp Thr Ala Ala<br>                        195                        200                        205 | 624 |
| gaa aat gac aga tgg cca tgg att cag ata aat ttg caa aga aaa atg<br>Glu Asn Asp Arg Trp Pro Trp Ile Gln Ile Asn Leu Gln Arg Lys Met<br>210                              215                        220 | 672 |
| aga gtc act ggt gtt att acc caa gga gca aaa agg att gga agc cca<br>Arg Val Thr Gly Val Ile Thr Gln Gly Ala Lys Arg Ile Gly Ser Pro<br>225                              230                        235                        240 | 720 |
| gag tac ata aaa tcc tac aaa att gcc tac agc aat gac ggg aag acc<br>Glu Tyr Ile Lys Ser Tyr Lys Ile Ala Tyr Ser Asn Asp Gly Lys Thr<br>                        245                        250                        255 | 768 |
| tgg gca atg tac aaa gta aaa ggc acc aat gaa gag atg gtc ttt cgt<br>Trp Ala Met Tyr Lys Val Lys Gly Thr Asn Glu Glu Met Val Phe Arg<br>                          260                        265                        270 | 816 |
| gga aat gtt gat aac aac aca cca tat gct aat tct ttc aca ccc cca<br>Gly Asn Val Asp Asn Asn Thr Pro Tyr Ala Asn Ser Phe Thr Pro Pro<br>                        275                        280                        285 | 864 |
| atc aaa gct cag tat gta aga ctc tac ccc caa att tgt cga agg cat<br>Ile Lys Ala Gln Tyr Val Arg Leu Tyr Pro Gln Ile Cys Arg Arg His<br>290                              295                        300 | 912 |
| tgt act tta aga atg gaa ctt ctt ggc tgt gag ctc tca ggc tgt tca<br>Cys Thr Leu Arg Met Glu Leu Leu Gly Cys Glu Leu Ser Gly Cys Ser<br>305                              310                        315                        320 | 960 |
| gaa cct ttg ggg atg aaa tca ggg cat ata caa gac tac cag atc act<br>Glu Pro Leu Gly Met Lys Ser Gly His Ile Gln Asp Tyr Gln Ile Thr<br>                        325                        330                        335 | 1008 |
| gcc tcc agc gtc ttc aga aca ctc aac atg gac atg ttt act tgg gaa<br>Ala Ser Ser Val Phe Arg Thr Leu Asn Met Asp Met Phe Thr Trp Glu<br>                        340                        345                        350 | 1056 |
| cca agg aaa gcc agg ctg gac aag caa ggc aaa gta aat gcc tgg act<br>Pro Arg Lys Ala Arg Leu Asp Lys Gln Gly Lys Val Asn Ala Trp Thr<br>355                              360                        365 | 1104 |

<210> SEQ ID NO 10
<211> LENGTH: 368
<212> TYPE: PRT
<213> ORGANISM: Mus musculus

<400> SEQUENCE: 10

Met Lys His Leu Val Ala Ala Trp Leu Leu Val Gly Leu Ser Leu Gly
1                 5                    10                   15

Val Pro Gln Phe Gly Lys Gly Asp Ile Cys Asn Pro Asn Pro Cys Glu
                 20                   25                   30

```
Asn Gly Gly Ile Cys Leu Ser Gly Leu Ala Asp Asp Ser Phe Ser Cys
        35                  40                  45
Glu Cys Pro Glu Gly Phe Ala Gly Pro Asn Cys Ser Ser Val Val Glu
 50                  55                  60
Val Ala Ser Asp Glu Glu Lys Pro Thr Ser Ala Gly Pro Cys Ile Pro
 65                  70                  75                  80
Asn Pro Cys His Asn Gly Gly Thr Cys Glu Ile Ser Glu Ala Tyr Arg
                 85                  90                  95
Gly Asp Thr Phe Ile Gly Tyr Val Cys Lys Cys Pro Arg Gly Phe Asn
            100                 105                 110
Gly Ile His Cys Gln His Asn Ile Asn Glu Cys Glu Ala Glu Pro Cys
            115                 120                 125
Arg Asn Gly Gly Ile Cys Thr Asp Leu Val Ala Asn Tyr Ser Cys Glu
130                 135                 140
Cys Pro Gly Glu Phe Met Gly Arg Asn Cys Gln Tyr Lys Cys Ser Gly
145                 150                 155                 160
Pro Leu Gly Ile Glu Gly Ile Ile Ser Asn Gln Gln Ile Thr Ala
                165                 170                 175
Ser Ser Thr His Arg Ala Leu Phe Gly Leu Arg Lys Trp Tyr Pro Tyr
            180                 185                 190
Tyr Ala Arg Leu Asn Lys Lys Gly Leu Ile Asn Ala Trp Thr Ala Ala
            195                 200                 205
Glu Asn Asp Arg Trp Pro Trp Ile Gln Ile Asn Leu Gln Arg Lys Met
    210                 215                 220
Arg Val Thr Gly Val Ile Thr Gln Gly Ala Lys Arg Ile Gly Ser Pro
225                 230                 235                 240
Glu Tyr Ile Lys Ser Tyr Lys Ile Ala Tyr Ser Asn Asp Gly Lys Thr
                245                 250                 255
Trp Ala Met Tyr Lys Val Lys Gly Thr Asn Glu Glu Met Val Phe Arg
            260                 265                 270
Gly Asn Val Asp Asn Asn Thr Pro Tyr Ala Asn Ser Phe Thr Pro Pro
            275                 280                 285
Ile Lys Ala Gln Tyr Val Arg Leu Tyr Pro Gln Ile Cys Arg Arg His
    290                 295                 300
Cys Thr Leu Arg Met Glu Leu Leu Gly Cys Glu Leu Ser Gly Cys Ser
305                 310                 315                 320
Glu Pro Leu Gly Met Lys Ser Gly His Ile Gln Asp Tyr Gln Ile Thr
                325                 330                 335
Ala Ser Ser Val Phe Arg Thr Leu Asn Met Asp Met Phe Thr Trp Glu
            340                 345                 350
Pro Arg Lys Ala Arg Leu Asp Lys Gln Gly Lys Val Asn Ala Trp Thr
            355                 360                 365
```

<210> SEQ ID NO 11
<211> LENGTH: 1155
<212> TYPE: DNA
<213> ORGANISM: Mus musculus
<220> FEATURE:
<221> NAME/KEY: CDS
<222> LOCATION: (1)..(1155)

<400> SEQUENCE: 11

```
atg aag cac ttg gta gca gcc tgg ctt ttg gtt gga ctc agc ctc ggg    48
Met Lys His Leu Val Ala Ala Trp Leu Leu Val Gly Leu Ser Leu Gly
 1               5                  10                  15
```

-continued

| | | |
|---|---|---|
| gtg ccc cag ttc ggc aaa ggt gac att tgc aac ccg aac ccc tgt gaa<br>Val Pro Gln Phe Gly Lys Gly Asp Ile Cys Asn Pro Asn Pro Cys Glu<br>20 25 30 | 96 |
| aat ggt ggc atc tgt ctg tca gga ctg gct gat gat tcc ttt tcc tgt<br>Asn Gly Gly Ile Cys Leu Ser Gly Leu Ala Asp Asp Ser Phe Ser Cys<br>35 40 45 | 144 |
| gag tgt cca gaa ggc ttc gca ggt ccg aac tgc tct agt gtt gtg gag<br>Glu Cys Pro Glu Gly Phe Ala Gly Pro Asn Cys Ser Ser Val Val Glu<br>50 55 60 | 192 |
| gtt gca tca gat gaa gaa aag cct act tca gca ggt ccc tgc atc cct<br>Val Ala Ser Asp Glu Glu Lys Pro Thr Ser Ala Gly Pro Cys Ile Pro<br>65 70 75 80 | 240 |
| aac cca tgc cat aac gga gga acc tgt gag ata agc gaa gcc tat cga<br>Asn Pro Cys His Asn Gly Gly Thr Cys Glu Ile Ser Glu Ala Tyr Arg<br>85 90 95 | 288 |
| gga gac aca ttc ata ggc tat gtt tgt aaa tgt cct cgg gga ttt aat<br>Gly Asp Thr Phe Ile Gly Tyr Val Cys Lys Cys Pro Arg Gly Phe Asn<br>100 105 110 | 336 |
| ggg att cac tgt cag cac aat ata aat gaa tgt gaa gct gag cct tgc<br>Gly Ile His Cys Gln His Asn Ile Asn Glu Cys Glu Ala Glu Pro Cys<br>115 120 125 | 384 |
| aga aat ggc gga ata tgt acc gac ctt gtt gct aac tac tct tgt gaa<br>Arg Asn Gly Gly Ile Cys Thr Asp Leu Val Ala Asn Tyr Ser Cys Glu<br>130 135 140 | 432 |
| tgc cca gga gaa ttt atg gga cga aat tgt caa tat aaa tgc tct ggg<br>Cys Pro Gly Glu Phe Met Gly Arg Asn Cys Gln Tyr Lys Cys Ser Gly<br>145 150 155 160 | 480 |
| cca ttg gga atc gaa ggt ggg atc ata tct aat cag caa atc aca gct<br>Pro Leu Gly Ile Glu Gly Gly Ile Ile Ser Asn Gln Gln Ile Thr Ala<br>165 170 175 | 528 |
| tca tct act cac cga gct ctt ttt gga ctc cgg aag tgg tat ccc tac<br>Ser Ser Thr His Arg Ala Leu Phe Gly Leu Arg Lys Trp Tyr Pro Tyr<br>180 185 190 | 576 |
| tat gct cga ctt aat aag aag ggc ctt ata aat gcc tgg aca gct gct<br>Tyr Ala Arg Leu Asn Lys Lys Gly Leu Ile Asn Ala Trp Thr Ala Ala<br>195 200 205 | 624 |
| gaa aat gac aga tgg cca tgg att cag ata aat ttg caa aga aaa atg<br>Glu Asn Asp Arg Trp Pro Trp Ile Gln Ile Asn Leu Gln Arg Lys Met<br>210 215 220 | 672 |
| aga gtc act ggt gtt att acc caa gga gca aaa agg att gga agc cca<br>Arg Val Thr Gly Val Ile Thr Gln Gly Ala Lys Arg Ile Gly Ser Pro<br>225 230 235 240 | 720 |
| gag tac ata aaa tcc tac aaa att gcc tac agc aat gac ggg aag acc<br>Glu Tyr Ile Lys Ser Tyr Lys Ile Ala Tyr Ser Asn Asp Gly Lys Thr<br>245 250 255 | 768 |
| tgg gca atg tac aaa gta aaa ggc acc aat gaa gag atg gtc ttt cgt<br>Trp Ala Met Tyr Lys Val Lys Gly Thr Asn Glu Glu Met Val Phe Arg<br>260 265 270 | 816 |
| gga aat gtt gat aac aac aca cca tat gct aat tct ttc aca ccc cca<br>Gly Asn Val Asp Asn Asn Thr Pro Tyr Ala Asn Ser Phe Thr Pro Pro<br>275 280 285 | 864 |
| atc aaa gct cag tat gta aga ctc tac ccc caa att tgt cga agg cat<br>Ile Lys Ala Gln Tyr Val Arg Leu Tyr Pro Gln Ile Cys Arg Arg His<br>290 295 300 | 912 |
| tgt act tta aga atg gaa ctt ctt ggc tgt gag ctc tca ggc tgt tca<br>Cys Thr Leu Arg Met Glu Leu Leu Gly Cys Glu Leu Ser Gly Cys Ser<br>305 310 315 320 | 960 |
| gaa cct ttg ggg atg aaa tca ggg cat ata caa gac tac cag atc act<br>Glu Pro Leu Gly Met Lys Ser Gly His Ile Gln Asp Tyr Gln Ile Thr<br>325 330 335 | 1008 |

-continued

```
gcc tcc agc gtc ttc aga aca ctc aac atg gac atg ttt act tgg gaa    1056
Ala Ser Ser Val Phe Arg Thr Leu Asn Met Asp Met Phe Thr Trp Glu
        340                 345                 350 cca agg aaa gcc agg ctg gac aag caa ggc aaa gta aat gcc tgg act    1104
Pro Arg Lys Ala Arg Leu Asp Lys Gln Gly Lys Val Asn Ala Trp Thr
            355                 360                 365 tcc ggc cat aac gac cag tca caa tgg tta cag gtt gat ctt ctt gtc    1152
Ser Gly His Asn Asp Gln Ser Gln Trp Leu Gln Val Asp Leu Leu Val
    370                 375                 380 cct                                                                1155
Pro
385

<210> SEQ ID NO 12
<211> LENGTH: 385
<212> TYPE: PRT
<213> ORGANISM: Mus musculus

<400> SEQUENCE: 12

Met Lys His Leu Val Ala Ala Trp Leu Leu Val Gly Leu Ser Leu Gly
1               5                   10                  15

Val Pro Gln Phe Gly Lys Gly Asp Ile Cys Asn Pro Asn Pro Cys Glu
            20                  25                  30

Asn Gly Gly Ile Cys Leu Ser Gly Leu Ala Asp Asp Ser Phe Ser Cys
        35                  40                  45

Glu Cys Pro Glu Gly Phe Ala Gly Pro Asn Cys Ser Ser Val Val Glu
    50                  55                  60

Val Ala Ser Asp Glu Glu Lys Pro Thr Ser Ala Gly Pro Cys Ile Pro
65                  70                  75                  80

Asn Pro Cys His Asn Gly Gly Thr Cys Glu Ile Ser Glu Ala Tyr Arg
                85                  90                  95

Gly Asp Thr Phe Ile Gly Tyr Val Cys Lys Cys Pro Arg Gly Phe Asn
            100                 105                 110

Gly Ile His Cys Gln His Asn Ile Asn Glu Cys Glu Ala Glu Pro Cys
        115                 120                 125

Arg Asn Gly Gly Ile Cys Thr Asp Leu Val Ala Asn Tyr Ser Cys Glu
    130                 135                 140

Cys Pro Gly Glu Phe Met Gly Arg Asn Cys Gln Tyr Lys Cys Ser Gly
145                 150                 155                 160

Pro Leu Gly Ile Glu Gly Gly Ile Ile Ser Asn Gln Gln Ile Thr Ala
                165                 170                 175

Ser Ser Thr His Arg Ala Leu Phe Gly Leu Arg Lys Trp Tyr Pro Tyr
            180                 185                 190

Tyr Ala Arg Leu Asn Lys Lys Gly Leu Ile Asn Ala Trp Thr Ala Ala
        195                 200                 205

Glu Asn Asp Arg Trp Pro Trp Ile Gln Ile Asn Leu Gln Arg Lys Met
    210                 215                 220

Arg Val Thr Gly Val Ile Thr Gln Gly Ala Lys Arg Ile Gly Ser Pro
225                 230                 235                 240

Glu Tyr Ile Lys Ser Tyr Lys Ile Ala Tyr Ser Asn Asp Gly Lys Thr
                245                 250                 255

Trp Ala Met Tyr Lys Val Lys Gly Thr Asn Glu Glu Met Val Phe Arg
            260                 265                 270

Gly Asn Val Asp Asn Asn Thr Pro Tyr Ala Asn Ser Phe Thr Pro Pro
        275                 280                 285
```

-continued

```
Ile Lys Ala Gln Tyr Val Arg Leu Tyr Pro Gln Ile Cys Arg Arg His
290                 295                 300

Cys Thr Leu Arg Met Glu Leu Leu Gly Cys Glu Leu Ser Gly Cys Ser
305                 310                 315                 320

Glu Pro Leu Gly Met Lys Ser Gly His Ile Gln Asp Tyr Gln Ile Thr
                325                 330                 335

Ala Ser Ser Val Phe Arg Thr Leu Asn Met Asp Met Phe Thr Trp Glu
            340                 345                 350

Pro Arg Lys Ala Arg Leu Asp Lys Gln Gly Lys Val Asn Ala Trp Thr
        355                 360                 365

Ser Gly His Asn Asp Gln Ser Gln Trp Leu Gln Val Asp Leu Leu Val
    370                 375                 380

Pro
385
```

<210> SEQ ID NO 13
<211> LENGTH: 789
<212> TYPE: DNA
<213> ORGANISM: Mus musculus
<220> FEATURE:
<221> NAME/KEY: CDS
<222> LOCATION: (1)..(789)

<400> SEQUENCE: 13

```
ata aat ttg caa aga aaa atg aga gtc act ggt gtt att acc caa gga     48
Ile Asn Leu Gln Arg Lys Met Arg Val Thr Gly Val Ile Thr Gln Gly
1               5                  10                  15 gca aaa agg att gga agc cca gag tac ata aaa tcc tac aaa att gcc     96
Ala Lys Arg Ile Gly Ser Pro Glu Tyr Ile Lys Ser Tyr Lys Ile Ala
                20                  25                  30 tac agc aat gac ggg aag acc tgg gca atg tac aaa gta aaa ggc acc    144
Tyr Ser Asn Asp Gly Lys Thr Trp Ala Met Tyr Lys Val Lys Gly Thr
            35                  40                  45 aat gaa gag atg gtc ttt cgt gga aat gtt gat aac aac aca cca tat    192
Asn Glu Glu Met Val Phe Arg Gly Asn Val Asp Asn Asn Thr Pro Tyr
        50                  55                  60 gct aat tct ttc aca ccc cca atc aaa gct cag tat gta aga ctc tac    240
Ala Asn Ser Phe Thr Pro Pro Ile Lys Ala Gln Tyr Val Arg Leu Tyr
65                  70                  75                  80 ccc caa att tgt cga agg cat tgt act tta aga atg gaa ctt ctt ggc    288
Pro Gln Ile Cys Arg Arg His Cys Thr Leu Arg Met Glu Leu Leu Gly
                85                  90                  95 tgt gag ctc tca ggc tgt tca gaa cct ttg ggg atg aaa tca ggg cat    336
Cys Glu Leu Ser Gly Cys Ser Glu Pro Leu Gly Met Lys Ser Gly His
                100                 105                 110 ata caa gac tac cag atc act gcc tcc agc gtc ttc aga aca ctc aac    384
Ile Gln Asp Tyr Gln Ile Thr Ala Ser Ser Val Phe Arg Thr Leu Asn
            115                 120                 125 atg gac atg ttt act tgg gaa cca agg aaa gcc agg ctg gac aag caa    432
Met Asp Met Phe Thr Trp Glu Pro Arg Lys Ala Arg Leu Asp Lys Gln
        130                 135                 140 ggc aaa gta aat gcc tgg act tcc ggc cat aac gac cag tca caa tgg    480
Gly Lys Val Asn Ala Trp Thr Ser Gly His Asn Asp Gln Ser Gln Trp
145                 150                 155                 160 tta cag gtt gat ctt ctt gtc cct act aag gtg aca ggc atc att aca    528
Leu Gln Val Asp Leu Leu Val Pro Thr Lys Val Thr Gly Ile Ile Thr
                165                 170                 175 caa gga gct aaa gat ttt ggt cac gtg cag ttt gtt ggg tca tac aaa    576
Gln Gly Ala Lys Asp Phe Gly His Val Gln Phe Val Gly Ser Tyr Lys
                180                 185                 190
```

```
cta gct tac agc aat gat gga gaa cac tgg atg gtg cac cag gat gaa      624
Leu Ala Tyr Ser Asn Asp Gly Glu His Trp Met Val His Gln Asp Glu
        195                 200                 205 aaa cag agg aaa gac aag gtt ttt caa ggc aat ttt gac aat gac act      672
Lys Gln Arg Lys Asp Lys Val Phe Gln Gly Asn Phe Asp Asn Asp Thr
210                 215                 220 cac agg aaa aat gtc atc gac cct ccc atc tat gca cga ttc ata aga      720
His Arg Lys Asn Val Ile Asp Pro Pro Ile Tyr Ala Arg Phe Ile Arg
225                 230                 235                 240 atc ctt cct tgg tcc tgg tat gga agg atc act ctg cgg tca gag ctg      768
Ile Leu Pro Trp Ser Trp Tyr Gly Arg Ile Thr Leu Arg Ser Glu Leu
                245                 250                 255 ctg ggc tgc gca gag gag gaa                                          789
Leu Gly Cys Ala Glu Glu Glu
        260
```

<210> SEQ ID NO 14
<211> LENGTH: 263
<212> TYPE: PRT
<213> ORGANISM: Mus musculus

<400> SEQUENCE: 14

```
Ile Asn Leu Gln Arg Lys Met Arg Val Thr Gly Val Ile Thr Gln Gly
1               5                   10                  15

Ala Lys Arg Ile Gly Ser Pro Glu Tyr Ile Lys Ser Tyr Lys Ile Ala
            20                  25                  30

Tyr Ser Asn Asp Gly Lys Thr Trp Ala Met Tyr Lys Val Lys Gly Thr
        35                  40                  45

Asn Glu Glu Met Val Phe Arg Gly Asn Val Asp Asn Asn Thr Pro Tyr
    50                  55                  60

Ala Asn Ser Phe Thr Pro Pro Ile Lys Ala Gln Tyr Val Arg Leu Tyr
65                  70                  75                  80

Pro Gln Ile Cys Arg Arg His Cys Thr Leu Arg Met Glu Leu Leu Gly
                85                  90                  95

Cys Glu Leu Ser Gly Cys Ser Glu Pro Leu Gly Met Lys Ser Gly His
            100                 105                 110

Ile Gln Asp Tyr Gln Ile Thr Ala Ser Ser Val Phe Arg Thr Leu Asn
        115                 120                 125

Met Asp Met Phe Thr Trp Glu Pro Arg Lys Ala Arg Leu Asp Lys Gln
    130                 135                 140

Gly Lys Val Asn Ala Trp Thr Ser Gly His Asn Asp Gln Ser Gln Trp
145                 150                 155                 160

Leu Gln Val Asp Leu Leu Val Pro Thr Lys Val Thr Gly Ile Ile Thr
                165                 170                 175

Gln Gly Ala Lys Asp Phe Gly His Val Gln Phe Val Gly Ser Tyr Lys
            180                 185                 190

Leu Ala Tyr Ser Asn Asp Gly Glu His Trp Met Val His Gln Asp Glu
        195                 200                 205

Lys Gln Arg Lys Asp Lys Val Phe Gln Gly Asn Phe Asp Asn Asp Thr
    210                 215                 220

His Arg Lys Asn Val Ile Asp Pro Pro Ile Tyr Ala Arg Phe Ile Arg
225                 230                 235                 240

Ile Leu Pro Trp Ser Trp Tyr Gly Arg Ile Thr Leu Arg Ser Glu Leu
                245                 250                 255

Leu Gly Cys Ala Glu Glu Glu
            260
```

<210> SEQ ID NO 15
<211> LENGTH: 306
<212> TYPE: DNA
<213> ORGANISM: Mus musculus
<220> FEATURE:
<221> NAME/KEY: CDS
<222> LOCATION: (1)..(306)

<400> SEQUENCE: 15

```
ata aat ttg caa aga aaa atg aga gtc act ggt gtt att acc caa gga        48
Ile Asn Leu Gln Arg Lys Met Arg Val Thr Gly Val Ile Thr Gln Gly
1               5                   10                  15 gca aaa agg att gga agc cca gag tac ata aaa tcc tac aaa att gcc        96
Ala Lys Arg Ile Gly Ser Pro Glu Tyr Ile Lys Ser Tyr Lys Ile Ala
            20                  25                  30 tac agc aat gac ggg aag acc tgg gca atg tac aaa gta aaa ggc acc       144
Tyr Ser Asn Asp Gly Lys Thr Trp Ala Met Tyr Lys Val Lys Gly Thr
        35                  40                  45 aat gaa gag atg gtc ttt cgt gga aat gtt gat aac aac aca cca tat       192
Asn Glu Glu Met Val Phe Arg Gly Asn Val Asp Asn Asn Thr Pro Tyr
    50                  55                  60 gct aat tct ttc aca ccc cca atc aaa gct cag tat gta aga ctc tac       240
Ala Asn Ser Phe Thr Pro Pro Ile Lys Ala Gln Tyr Val Arg Leu Tyr
65                  70                  75                  80 ccc caa att tgt cga agg cat tgt act tta aga atg gaa ctt ctt ggc       288
Pro Gln Ile Cys Arg Arg His Cys Thr Leu Arg Met Glu Leu Leu Gly
                85                  90                  95 tgt gag ctc tca ggc tgt                                               306
Cys Glu Leu Ser Gly Cys
            100
```

<210> SEQ ID NO 16
<211> LENGTH: 102
<212> TYPE: PRT
<213> ORGANISM: Mus musculus

<400> SEQUENCE: 16

```
Ile Asn Leu Gln Arg Lys Met Arg Val Thr Gly Val Ile Thr Gln Gly
1               5                   10                  15

Ala Lys Arg Ile Gly Ser Pro Glu Tyr Ile Lys Ser Tyr Lys Ile Ala
            20                  25                  30

Tyr Ser Asn Asp Gly Lys Thr Trp Ala Met Tyr Lys Val Lys Gly Thr
        35                  40                  45

Asn Glu Glu Met Val Phe Arg Gly Asn Val Asp Asn Asn Thr Pro Tyr
    50                  55                  60

Ala Asn Ser Phe Thr Pro Pro Ile Lys Ala Gln Tyr Val Arg Leu Tyr
65                  70                  75                  80

Pro Gln Ile Cys Arg Arg His Cys Thr Leu Arg Met Glu Leu Leu Gly
                85                  90                  95

Cys Glu Leu Ser Gly Cys
            100
```

<210> SEQ ID NO 17
<211> LENGTH: 678
<212> TYPE: DNA
<213> ORGANISM: Mus musculus
<220> FEATURE:
<221> NAME/KEY: CDS
<222> LOCATION: (1)..(678)

<400> SEQUENCE: 17

```
tgt gaa gct gag cct tgc aga aat ggc gga ata tgt acc gac ctt gtt      48
Cys Glu Ala Glu Pro Cys Arg Asn Gly Gly Ile Cys Thr Asp Leu Val
1               5                   10                  15 gct aac tac tct tgt gaa tgc cca gga gaa ttt atg gga cga aat tgt      96
Ala Asn Tyr Ser Cys Glu Cys Pro Gly Glu Phe Met Gly Arg Asn Cys
            20                  25                  30 caa tat aaa tgc tct ggg cca ttg gga atc gaa ggt ggg atc ata tct     144
Gln Tyr Lys Cys Ser Gly Pro Leu Gly Ile Glu Gly Gly Ile Ile Ser
        35                  40                  45 aat cag caa atc aca gct tca tct act cac cga gct ctt ttt gga ctc     192
Asn Gln Gln Ile Thr Ala Ser Ser Thr His Arg Ala Leu Phe Gly Leu
50                  55                  60 cgg aag tgg tat ccc tac tat gct cga ctt aat aag aag ggc ctt ata     240
Arg Lys Trp Tyr Pro Tyr Tyr Ala Arg Leu Asn Lys Lys Gly Leu Ile
65                  70                  75                  80 aat gcc tgg aca gct gct gaa aat gac aga tgg cca tgg att cag ata     288
Asn Ala Trp Thr Ala Ala Glu Asn Asp Arg Trp Pro Trp Ile Gln Ile
                85                  90                  95 aat ttg caa aga aaa atg aga gtc act ggt gtt att acc caa gga gca     336
Asn Leu Gln Arg Lys Met Arg Val Thr Gly Val Ile Thr Gln Gly Ala
            100                 105                 110 aaa agg att gga agc cca gag tac ata aaa tcc tac aaa att gcc tac     384
Lys Arg Ile Gly Ser Pro Glu Tyr Ile Lys Ser Tyr Lys Ile Ala Tyr
        115                 120                 125 agc aat gac ggg aag acc tgg gca atg tac aaa gta aaa ggc acc aat     432
Ser Asn Asp Gly Lys Thr Trp Ala Met Tyr Lys Val Lys Gly Thr Asn
    130                 135                 140 gaa gag atg gtc ttt cgt gga aat gtt gat aac aac aca cca tat gct     480
Glu Glu Met Val Phe Arg Gly Asn Val Asp Asn Asn Thr Pro Tyr Ala
145                 150                 155                 160 aat tct ttc aca ccc cca atc aaa gct cag tat gta aga ctc tac ccc     528
Asn Ser Phe Thr Pro Pro Ile Lys Ala Gln Tyr Val Arg Leu Tyr Pro
                165                 170                 175 caa att tgt cga agg cat tgt act tta aga atg gaa ctt ctt ggc tgt     576
Gln Ile Cys Arg Arg His Cys Thr Leu Arg Met Glu Leu Leu Gly Cys
            180                 185                 190 gag ctc tca ggc tgt tca gaa cct ttg ggg atg aaa tca ggg cat ata     624
Glu Leu Ser Gly Cys Ser Glu Pro Leu Gly Met Lys Ser Gly His Ile
        195                 200                 205 caa gac tac cag atc act gcc tcc agc gtc ttc aga aca ctc aac atg     672
Gln Asp Tyr Gln Ile Thr Ala Ser Ser Val Phe Arg Thr Leu Asn Met
    210                 215                 220 gac atg                                                              678
Asp Met
225
```

<210> SEQ ID NO 18
<211> LENGTH: 226
<212> TYPE: PRT
<213> ORGANISM: Mus musculus

<400> SEQUENCE: 18

```
Cys Glu Ala Glu Pro Cys Arg Asn Gly Gly Ile Cys Thr Asp Leu Val
1               5                   10                  15

Ala Asn Tyr Ser Cys Glu Cys Pro Gly Glu Phe Met Gly Arg Asn Cys
            20                  25                  30

Gln Tyr Lys Cys Ser Gly Pro Leu Gly Ile Glu Gly Gly Ile Ile Ser
        35                  40                  45
```

```
Asn Gln Gln Ile Thr Ala Ser Ser Thr His Arg Ala Leu Phe Gly Leu
    50                  55                  60
Arg Lys Trp Tyr Pro Tyr Tyr Ala Arg Leu Asn Lys Lys Gly Leu Ile
65                  70                  75                  80
Asn Ala Trp Thr Ala Ala Glu Asn Asp Arg Trp Pro Trp Ile Gln Ile
                85                  90                  95
Asn Leu Gln Arg Lys Met Arg Val Thr Gly Val Ile Thr Gln Gly Ala
            100                 105                 110
Lys Arg Ile Gly Ser Pro Glu Tyr Ile Lys Ser Tyr Lys Ile Ala Tyr
        115                 120                 125
Ser Asn Asp Gly Lys Thr Trp Ala Met Tyr Lys Val Lys Gly Thr Asn
    130                 135                 140
Glu Glu Met Val Phe Arg Gly Asn Val Asp Asn Asn Thr Pro Tyr Ala
145                 150                 155                 160
Asn Ser Phe Thr Pro Pro Ile Lys Ala Gln Tyr Val Arg Leu Tyr Pro
                165                 170                 175
Gln Ile Cys Arg Arg His Cys Thr Leu Arg Met Glu Leu Leu Gly Cys
            180                 185                 190
Glu Leu Ser Gly Cys Ser Glu Pro Leu Gly Met Lys Ser Gly His Ile
        195                 200                 205
Gln Asp Tyr Gln Ile Thr Ala Ser Ser Val Phe Arg Thr Leu Asn Met
    210                 215                 220
Asp Met
225

<210> SEQ ID NO 19
<211> LENGTH: 285
<212> TYPE: DNA
<213> ORGANISM: Mus musculus
<220> FEATURE:
<221> NAME/KEY: CDS
<222> LOCATION: (1)..(285)

<400> SEQUENCE: 19 tgt gaa gct gag cct tgc aga aat ggc gga ata tgt acc gac ctt gtt       48
Cys Glu Ala Glu Pro Cys Arg Asn Gly Gly Ile Cys Thr Asp Leu Val
1               5                   10                  15 gct aac tac tct tgt gaa tgc cca gga gaa ttt atg gga cga aat tgt       96
Ala Asn Tyr Ser Cys Glu Cys Pro Gly Glu Phe Met Gly Arg Asn Cys
            20                  25                  30 caa tat aaa tgc tct ggg cca ttg gga atc gaa ggt ggg atc ata tct      144
Gln Tyr Lys Cys Ser Gly Pro Leu Gly Ile Glu Gly Gly Ile Ile Ser
        35                  40                  45 aat cag caa atc aca gct tca tct act cac cga gct ctt ttt gga ctc      192
Asn Gln Gln Ile Thr Ala Ser Ser Thr His Arg Ala Leu Phe Gly Leu
    50                  55                  60 cgg aag tgg tat ccc tac tat gct cga ctt aat aag aag ggc ctt ata      240
Arg Lys Trp Tyr Pro Tyr Tyr Ala Arg Leu Asn Lys Lys Gly Leu Ile
65                  70                  75                  80 aat gcc tgg aca gct gct gaa aat gac aga tgg cca tgg att cag           285
Asn Ala Trp Thr Ala Ala Glu Asn Asp Arg Trp Pro Trp Ile Gln
                85                  90                  95

<210> SEQ ID NO 20
<211> LENGTH: 95
<212> TYPE: PRT
<213> ORGANISM: Mus musculus
```

```
<400> SEQUENCE: 20

Cys Glu Ala Glu Pro Cys Arg Asn Gly Gly Ile Cys Thr Asp Leu Val
1               5                   10                  15

Ala Asn Tyr Ser Cys Glu Cys Pro Gly Glu Phe Met Gly Arg Asn Cys
            20                  25                  30

Gln Tyr Lys Cys Ser Gly Pro Leu Gly Ile Glu Gly Gly Ile Ile Ser
        35                  40                  45

Asn Gln Gln Ile Thr Ala Ser Ser Thr His Arg Ala Leu Phe Gly Leu
    50                  55                  60

Arg Lys Trp Tyr Pro Tyr Tyr Ala Arg Leu Asn Lys Lys Gly Leu Ile
65                  70                  75                  80

Asn Ala Trp Thr Ala Ala Glu Asn Asp Arg Trp Pro Trp Ile Gln
                85                  90                  95

<210> SEQ ID NO 21
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 21 ttt act tgg gaa cca agg aaa gcc agg ctg gac aag caa ggc aaa gta        48
Phe Thr Trp Glu Pro Arg Lys Ala Arg Leu Asp Lys Gln Gly Lys Val
1               5                   10                  15 aat gcc tgg act tcc ggc cat aac gac cag tca caa tgg tta cag gtt       96
Asn Ala Trp Thr Ser Gly His Asn Asp Gln Ser Gln Trp Leu Gln Val
            20                  25                  30 gat ctt ctt gtc cct act aag gtg aca ggc atc att aca caa gga gct      144
Asp Leu Leu Val Pro Thr Lys Val Thr Gly Ile Ile Thr Gln Gly Ala
        35                  40                  45 aaa gat ttt ggt cac gtg cag ttt gtt ggg tca tac aaa cta gct tac      192
Lys Asp Phe Gly His Val Gln Phe Val Gly Ser Tyr Lys Leu Ala Tyr
    50                  55                  60 agc aat gat gga gaa cac tgg atg gtg cac cag gat gaa aaa cag agg      240
Ser Asn Asp Gly Glu His Trp Met Val His Gln Asp Glu Lys Gln Arg
65                  70                  75                  80 aaa gac aag gtt ttt caa ggc aat ttt gac aat gac act cac agg aaa      288
Lys Asp Lys Val Phe Gln Gly Asn Phe Asp Asn Asp Thr His Arg Lys
                85                  90                  95 aat gtc atc gac cct ccc atc tat gca cga ttc ata aga atc ctt cct      336
Asn Val Ile Asp Pro Pro Ile Tyr Ala Arg Phe Ile Arg Ile Leu Pro
            100                 105                 110 tgg tcc tgg tat gga agg atc act ctg cgg tca gag ctg ctg ggc tgc      384
Trp Ser Trp Tyr Gly Arg Ile Thr Leu Arg Ser Glu Leu Leu Gly Cys
        115                 120                 125 gca gag gag gaa                                                      396
Ala Glu Glu Glu
    130

<210> SEQ ID NO 22
<211> LENGTH: 132
<212> TYPE: PRT
<213> ORGANISM: Mus musculus

<400> SEQUENCE: 22

Phe Thr Trp Glu Pro Arg Lys Ala Arg Leu Asp Lys Gln Gly Lys Val
1               5                   10                  15
```

```
Asn Ala Trp Thr Ser Gly His Asn Asp Gln Ser Gln Trp Leu Gln Val
             20                  25                  30

Asp Leu Leu Val Pro Thr Lys Val Thr Gly Ile Ile Thr Gln Gly Ala
         35                  40                  45

Lys Asp Phe Gly His Val Gln Phe Val Gly Ser Tyr Lys Leu Ala Tyr
     50                  55                  60

Ser Asn Asp Gly Glu His Trp Met Val His Gln Asp Glu Lys Gln Arg
 65                  70                  75                  80

Lys Asp Lys Val Phe Gln Gly Asn Phe Asp Asn Asp Thr His Arg Lys
                 85                  90                  95

Asn Val Ile Asp Pro Pro Ile Tyr Ala Arg Phe Ile Arg Ile Leu Pro
            100                 105                 110

Trp Ser Trp Tyr Gly Arg Ile Thr Leu Arg Ser Glu Leu Leu Gly Cys
            115                 120                 125

Ala Glu Glu Glu
        130

<210> SEQ ID NO 23
<211> LENGTH: 678
<212> TYPE: DNA
<213> ORGANISM: Homo sapiens
<220> FEATURE:
<221> NAME/KEY: CDS
<222> LOCATION: (1)..(678)

<400> SEQUENCE: 23 tgc gaa gtt gag cct tgc aaa aat ggt gga ata tgt aca gat ctt gtt     48
Cys Glu Val Glu Pro Cys Lys Asn Gly Gly Ile Cys Thr Asp Leu Val
 1               5                  10                  15 gct aac tat tcc tgt gag tgc cca ggc gaa ttt atg gga aga aat tgt     96
Ala Asn Tyr Ser Cys Glu Cys Pro Gly Glu Phe Met Gly Arg Asn Cys
             20                  25                  30 caa tac aaa tgc tca ggc cca ctg gga att gaa ggt gga att ata tca    144
Gln Tyr Lys Cys Ser Gly Pro Leu Gly Ile Glu Gly Gly Ile Ile Ser
         35                  40                  45 aac cag caa atc aca gct tcc tct act cac cga gct ctt ttt gga ctc    192
Asn Gln Gln Ile Thr Ala Ser Ser Thr His Arg Ala Leu Phe Gly Leu
 50                  55                  60 caa aaa tgg tat ccc tac tat gca cgt ctt aat aag aag ggg ctt ata    240
Gln Lys Trp Tyr Pro Tyr Tyr Ala Arg Leu Asn Lys Lys Gly Leu Ile
 65                  70                  75                  80 aat gcg tgg aca gct gca gaa aat gac aga tgg ccg tgg att cag ata    288
Asn Ala Trp Thr Ala Ala Glu Asn Asp Arg Trp Pro Trp Ile Gln Ile
                 85                  90                  95 aat ttg caa agg aaa atg aga gtt act ggt gtg att acc caa gga gcc    336
Asn Leu Gln Arg Lys Met Arg Val Thr Gly Val Ile Thr Gln Gly Ala
            100                 105                 110 aag agg att gga agc cca gag tat ata aaa tcc tac aaa att gcc tac    384
Lys Arg Ile Gly Ser Pro Glu Tyr Ile Lys Ser Tyr Lys Ile Ala Tyr
            115                 120                 125 agt aat gat gga aag act tgg gca atg tac aaa gtg aaa ggc acc aat    432
Ser Asn Asp Gly Lys Thr Trp Ala Met Tyr Lys Val Lys Gly Thr Asn
130                 135                 140 gaa gac atg gtg ttt cgt gga aac att gat aac aac act cca tat gct    480
Glu Asp Met Val Phe Arg Gly Asn Ile Asp Asn Asn Thr Pro Tyr Ala
145                 150                 155                 160 aac tct ttc aca ccc ccc ata aaa gct cag tat gta aga ctc tat ccc    528
Asn Ser Phe Thr Pro Pro Ile Lys Ala Gln Tyr Val Arg Leu Tyr Pro
                165                 170                 175
```

```
caa gtt tgt cga aga cat tgc act ttg cga atg gaa ctt ctt ggc tgt      576
Gln Val Cys Arg Arg His Cys Thr Leu Arg Met Glu Leu Leu Gly Cys
        180                 185                 190 gaa ctg tcg ggt tgt tct gag cct ctg ggt atg aaa tca gga cat ata      624
Glu Leu Ser Gly Cys Ser Glu Pro Leu Gly Met Lys Ser Gly His Ile
    195                 200                 205 caa gac tat cag atc act gcc tcc agc atc ttc aga acg ctc aac atg      672
Gln Asp Tyr Gln Ile Thr Ala Ser Ser Ile Phe Arg Thr Leu Asn Met
210                 215                 220 gac atg                                                              678
Asp Met
225

<210> SEQ ID NO 24
<211> LENGTH: 226
<212> TYPE: PRT
<213> ORGANISM: Homo sapiens

<400> SEQUENCE: 24

Cys Glu Val Glu Pro Cys Lys Asn Gly Gly Ile Cys Thr Asp Leu Val
1               5                   10                  15

Ala Asn Tyr Ser Cys Glu Cys Pro Gly Glu Phe Met Gly Arg Asn Cys
            20                  25                  30

Gln Tyr Lys Cys Ser Gly Pro Leu Gly Ile Glu Gly Gly Ile Ile Ser
        35                  40                  45

Asn Gln Gln Ile Thr Ala Ser Ser Thr His Arg Ala Leu Phe Gly Leu
    50                  55                  60

Gln Lys Trp Tyr Pro Tyr Tyr Ala Arg Leu Asn Lys Lys Gly Leu Ile
65                  70                  75                  80

Asn Ala Trp Thr Ala Ala Glu Asn Asp Arg Trp Pro Trp Ile Gln Ile
                85                  90                  95

Asn Leu Gln Arg Lys Met Arg Val Thr Gly Val Ile Thr Gln Gly Ala
            100                 105                 110

Lys Arg Ile Gly Ser Pro Glu Tyr Ile Lys Ser Tyr Lys Ile Ala Tyr
        115                 120                 125

Ser Asn Asp Gly Lys Thr Trp Ala Met Tyr Lys Val Lys Gly Thr Asn
    130                 135                 140

Glu Asp Met Val Phe Arg Gly Asn Ile Asp Asn Asn Thr Pro Tyr Ala
145                 150                 155                 160

Asn Ser Phe Thr Pro Pro Ile Lys Ala Gln Tyr Val Arg Leu Tyr Pro
                165                 170                 175

Gln Val Cys Arg Arg His Cys Thr Leu Arg Met Glu Leu Leu Gly Cys
            180                 185                 190

Glu Leu Ser Gly Cys Ser Glu Pro Leu Gly Met Lys Ser Gly His Ile
        195                 200                 205

Gln Asp Tyr Gln Ile Thr Ala Ser Ser Ile Phe Arg Thr Leu Asn Met
    210                 215                 220

Asp Met
225

<210> SEQ ID NO 25
<211> LENGTH: 26
<212> TYPE: DNA
<213> ORGANISM: Artificial sequence
<220> FEATURE:
<223> OTHER INFORMATION: synthetic DNA
```

-continued

```
<400> SEQUENCE: 25
aaagatctaa cccgaacccc tgtgaa                                    26

<210> SEQ ID NO 26
<211> LENGTH: 24
<212> TYPE: DNA
<213> ORGANISM: Artificial sequence
<220> FEATURE:
<223> OTHER INFORMATION: synthetic DNA

<400> SEQUENCE: 26
aactcgagca tttgtggatg tgcg                                      24
```